US012758587B2

(12) United States Patent
Hare et al.

(10) Patent No.: US 12,758,587 B2
(45) Date of Patent: Oct. 13, 2026

(54) BONE MARROW DERIVED CD271 PRECURSOR CELLS FOR CARDIAC REPAIR

(71) Applicant: JMHMD HOLDINGS LLC, Miami, FL (US)

(72) Inventors: Joshua M. Hare, Miami Beach, FL (US); Ian K. McNiece, Coral Gables, FL (US)

(73) Assignee: JMHMD Holdings LLC, Miami, FL (US)

( * ) Notice: Subject to any disclaimer, the term of this patent is extended or adjusted under 35 U.S.C. 154(b) by 158 days.

(21) Appl. No.: 17/811,418

(22) Filed: Jul. 8, 2022

(65) Prior Publication Data

US 2023/0071551 A1 Mar. 9, 2023

Related U.S. Application Data

(63) Continuation of application No. 15/720,373, filed on Sep. 29, 2017, now abandoned, which is a continuation of application No. 13/819,154, filed as application No. PCT/US2011/049542 on Aug. 29, 2011, now abandoned.

(60) Provisional application No. 61/377,661, filed on Aug. 27, 2010.

(51) Int. Cl.
*A61K 35/28* (2015.01)

(52) U.S. Cl.
CPC .................................... *A61K 35/28* (2013.01)

(58) Field of Classification Search
None
See application file for complete search history.

(56) References Cited

U.S. PATENT DOCUMENTS

| | | | | |
|---|---|---|---|---|
| 2002/0142457 | A1* | 10/2002 | Umezawa | C12N 5/069 435/366 |
| 2003/0003572 | A1 | 1/2003 | Anderson et al. | |
| 2005/0129663 | A1* | 6/2005 | Fulga | A61K 39/464 435/372 |
| 2009/0304643 | A1 | 12/2009 | Khurgel et al. | |
| 2009/0324609 | A1 | 12/2009 | Lodie et al. | |
| 2010/0215722 | A1 | 8/2010 | Bhasin et al. | |
| 2010/0260721 | A1 | 10/2010 | Mcgonagie et al. | |
| 2011/0177041 | A1 | 7/2011 | Nakashima et al. | |
| 2011/0182866 | A1 | 7/2011 | Mcniece | |
| 2013/0183272 | A1 | 7/2013 | Kimbrel et al. | |
| 2014/0023621 | A1 | 1/2014 | Hare et al. | |

FOREIGN PATENT DOCUMENTS

| | | | |
|---|---|---|---|
| WO | 2009/140452 | A2 | 11/2009 |
| WO | 2010/056341 | A2 | 5/2010 |
| WO | 2012/027740 | A1 | 3/2012 |
| WO | 2013/005053 | A2 | 1/2013 |
| WO | 2013/033043 | A1 | 3/2013 |

OTHER PUBLICATIONS

Amado et al., PNAS, vol. 102, No. 32, pp. 11474-11479, Aug. 9, 2005 (Year: 2005).*
Ghodsizad et al., Heart, 2009;95:27-35 (Year: 2009).*
Hombrebueno et al., TVST 2014, vol. 3, No. 2, Article 3, pp. 1-9 (Year: 2014).*
Boehar et al., Journal of the American College of Cardiology, vol. 56, No. 16, 2010, pp. 1287-1297 (Year: 2010).*
Fukuhara et al., Cell Transplantation, vol. 13, pp. 741-747, 2004 (Year: 2004).*
Martinez et al., Bone Marrow Transplantation 24, 1273-1278 (1999), Abstract (Year: 1999).*
Yong et al., British Journal of Haematology, 1996, 94, 40-47 (Year: 1996).*
Miltenyi Biotec CD271 MicroBead Kit Protocol, 5 pages, retrieved from the internet: document_vqvj71bnap7i91ar59tlqrm024 (Feb. 11, 2026). (Year: 2026).*
Miltenyi Biotec MACS Cell Pre-Enrichment for flow sorting and analysis, 10 pages, retrieved from the internet (Feb. 11, 2026): https:// static.miltenyibiotec.com/asset/150655405641/document_61ufne1r813nv4reapbnjtc45s?content-disposition=inline (Year: 2026).*
You Tube demonstration for Miltenyi Biotec, How to Isolate Cells in 3 Easy Steps using MACS MicroBeads, available online at https://www.youtube.com/watch?v=JQQIXL004uw&t=8s (Feb. 11, 2026) (Year: 2026).*
Mund et al., Cancer Res 2005; 65: (16), Aug. 15, 2005, pp. 7086-7090 (Year: 2005).*
Shiota et al., Experimental Cell Research 313 (2007) 1008-1023 (Year: 2007).*
"Related terms: inflammation of the wall of the heart, myocardium," Texas Heart Institute, 2 pages (2015). [Retrieved from the Internet Jan. 29, 2016: <URL: http://www.texasheart.org/HIC/Topics/Cond/myocard.cfm>]. [Author Unknown].
Aoyagi et al., "Significance of CD271 in Bone Marrow Mesenchymal Stem Cells-Changes by Cryopreservation," The Journal of Craniofacial Surgery, 21(3):666-678 (2010).
Buhring, H et al., "Novel Markers for the Prospective Isolation of Human MSC," Annals of the New York Academy of Sciences, 1106:262-271 (2007).
Davani et al., "Mesenchymal Progenitor Cells Differentiate Into an Endothelial Phenotype, Enhance Vascular Density, and Improve Heart Function in a Rat Cellular Cardiomyoplasty Mode," Circulation Journal of the American Heart Association, pp. 1008 (Suppl. 1):11253-11258 (2003).
Davani et al., "Mesenchymal progenitor cells differentiate into an endothelial phenotype, enhance vascular density, and improve heart function in a rat cellular cardiomyoplasty model," Circulation Journal of the American Heart Association, 108 (Suppl. 2):II-253-II-258 (2003).

(Continued)

*Primary Examiner* — Evelyn Y Pyla
(74) *Attorney, Agent, or Firm* — Buchanan Ingersoll & Rooney PC

(57) ABSTRACT

Methods for the isolation of $CD271^+$ stem cell populations are important in the prevention or treatment of cardiovascular diseases and repair of cardiac tissue. The methods are applicable to stem cells from different sources and can be used to treat or prevent diseases or repair of tissues elsewhere in the organism's body.

19 Claims, 9 Drawing Sheets
(4 of 9 Drawing Sheet(s) Filed in Color)

(56) References Cited

OTHER PUBLICATIONS

EP Application No. 11820774.5, Supplementary European Search Report, issued Jan. 2, 2014.
Flores-Torales et al., "The CD271 expression could be alone for establisher phenotypic marker in Bone Marrow derived mesenchymal stem cells," Folia Histochemica et Cytobiologica/Polish Academy of Sciences, Polish Histochemical and Cytochemical Society, 48(4):682-686 (2010).
Ghodsizad et al., "Application of CD271+ human bone marrow-derived: Stem cells for ischaemic heart disease therapy," European Cardiology 2011 Touch Briefings GBR, 7(4):280-282 (2011).
Gnecchi, et al., "Evidence supporting paracrine hypothesis for Akt-modified mesenchymal stem cell-mediated cardiac protection and functional improvement," FASEB J., 20(6):661-669 (2006).
Herrmann et al., "Postinfarct intramyocardial injection of mesenchymal stem cells pretreated with TGF-a improves acute myocardial function," Am. J. Physiol Regul. Intergr. Comp. Physiol. 299:R371-R378 (2010).
Iso et al., "CD271 Identifies Human Bone Marrow Stem/Progenitor Cells with a Proangiogenic Potential and Circulating Progenitor Cells Mobilized after Acute Myocardial Infarction," Journal of the American College of Cardiology, Elsevier, NY, USA, 55(10A), 1 page (2010).
Iso et al., "Human Bone Marrow Progenitor Cells Derived From CD271+ Stem Cells Secrete Factors That Improve Cardiac Function After Myocardial Infarction and Activate Adult Resident Cardiac Progenitors," Circulation, 122: Abstract No. 13854 (2010). [Retrieved from the Internet Jan. 21, 2014: <URL: http://circ.ahajournals.org/cgi/content/meeting_abstract/122/21_Meeting Abstracts/A13854>].
Jarocha et al., "Adventage of mesenchymal stem cells (MSC) expansion directly from purified bone marrow CD105+ and CD271+ cells," Folia Histochemica et Cytobiologica, 46(3):307-314, Polish Histochemical et Cytochemical Society (2008).
Kuci et al., "CD271 antigen defines a subset of multipotent stromal cells with immunosuppressive and lymphohematopoietic engraftment-promoting properties," Haematologica, 95(4):651-659, Ferrata Storti Foundation (2010).
Machler et al., "Preoperative myocardial cell damage in patients with unstable angina undergoing coronary artery bypass graft surgery," Anesthesiology, 81(6):1324-1331 (1994). Abstract only. [Retrieved from the Internet Jan. 29, 2016: <URL: http://www.ncbi.nlm.nih.gov/pubmed/7992899>].
Mirotsou, et al., "Paracrine mechanisms of stem cell reparative and regenerative actions in the heart," J Mol Cell Cardiol., 50(2):280-289 (2011).
Nesselmann et al., "Mesenchymal stem cells and cardiac repair," J. Cell. Mol. Med., 12(5B):1795-1810, Foundation for Cellular and Molecular Medicine, Blackwell Publishing Ltd. (2008).
Quevedo et al., "Allogeneic mesenchymal stem cells restore cardiac function in chronic ischemic cardiomyopathy via trilineage differentiating capacity," Proceedings of the National Academy of Sciences of the United States of America, 106(33):14022-14027 (2009).
Riegler et al., "Human Engineered Heart Muscles Engraft and Survive Long Term in a Rodent Myocardial Infarction Model," Circ. Res., 117:720-730, DOI:10.1161/CIRCRESAHA.115.306985 (2015).
Romero-Bermejo et al., "Sepsis-induced Cardiomyopathy," Current Cardiology Reviews, 7:163-183 (2011).
Schuleri et al., "Autologous Mesenchymal Stem Cells Produce Reverse Remodelling in Chronic Ischaemic Cardiomyopathy," Eur. Heart J., 30(22):2722-2732 (2009).
Toma et al., "Human Mesenchymal Stem Cells Differentiate to a Cardiomyocyte Phenotype in the Adult Murine Heart," Circulation, 105:93-98, American Heart Association (2002). [Retrieved from the Internet Jan. 20, 2014: <URL: http://circ.ahajournals.org>].
Vela, et al., "Histopathological Study of Healing After Allogenic Mesenchymal Stem Cell Delivery in Myocardial Infarction in Dogs," Journal of Histochemistry & Cytochemistry, 57(2):167-176 (2009).
Wang, H-S. et al., "Mesenchymal Stem Cells in the Wharton's Jelly of the Human Umbilical Cord," Stem Cells, 22:1330-1337 (2004).
Williams et ano, "Mesenchymal Stem Cells: Biology, Pathophysiology, Translational Findings, and Therapeutic Implications for Cardiac Disease," Circ Res., 109:923-940, American Heart Association (2011). [Retrieved from the Internet Jan. 20, 2014: <URL: http://circres.ahajournals.org>].
WIPO Application No. PCT/US2011/049542, International Preliminary Report on Patentability, issued Mar. 5, 2013.
WIPO Application No. PCT/US2011/049542, International Search Report, mailed Feb. 1, 2012.
WIPO Application No. PCT/US2011/049542, Written Opinion of the International Searching Authority, mailed Feb. 1, 2012.
Xu et al., "Mesenchymal Stem Cells from Adult Human Bone Marrow Differentiate into a Cardiomyocyte Phenotype In Vitro," Exp. Biol. Med., 229(7):623-631, Society for Experimental Biology and Medicine, China (2004). [Retrieved from the Internet Jan. 20, 2014: <URL: http://www.ebm.sagepub.com>].
U.S. Appl. No. 13/819,154, Final Office Action mailed Mar. 30, 2017.
U.S. Appl. No. 13/819,154, Final Office Action mailed Oct. 20, 2015.
U.S. Appl. No. 13/819,154, Non-Final Office Action mailed Mar. 18, 2015.
U.S. Appl. No. 13/819,154, Non-Final Office Action mailed Jun. 15, 2016.
U.S. Appl. No. 13/819,154, Requirement for Restriction/Election mailed Oct. 31, 2014.

* cited by examiner

BONE MARROW DERIVED CD271 PRECURSOR CELLS FOR CARDIAC REPAIR

CROSS-REFERENCE TO RELATED APPLICATIONS

This application is a continuation of U.S. patent application Ser. No. 15/720,373 filed Sep. 29, 2017, which is a continuation of U.S. patent application Ser. No. 13/819,154 filed Oct. 10, 2013, which is a U.S. National Stage entry of PCT/US11/49542 filed Aug. 29, 2011, which claims priority to U.S. Provisional Application No. 61/377,661 filed Aug. 27 2010, the entire contents of which are incorporate herein by reference.

FIELD OF THE INVENTION

Embodiments of the invention are directed to methods for treating cardiovascular diseases using bone marrow derived mesenchymal-precursor cells.

BACKGROUND

Heart failure is responsible for $33.2 billion in direct and indirect costs to the US healthcare system (1, 2) and the majority of patients with this diagnosis have scarred myocardium from previous MI. Left ventricular function is the most important determinant of survival and quality of life in patients who have suffered a myocardial infarction (MI) (1, 3). The myocardium has very limited regenerative potential after infarction and a major quest in medicine presently is that of cell-based tissue regeneration. This quest holds the promise of transforming the treatment of numerous chronic illnesses. In the area of chronic ischemic cardiomyopathy (a disorder affecting more than 4 million Americans), a successful cell-based therapeutic will have an enormous impact on patient morbidity and mortality, and reduce the societal burdens of this disorder. In order to advance this field, there have been significant attempts to achieve a successful cell therapeutic over the past half-decade, and strategies employing cells derived from bone marrow have been tested in early clinical trials (4, 5). These trials have done much to advance understanding of cell delivery methods and to establish safety profiles; however, an ideal cell source remains to be fully established.

SUMMARY

This Summary is provided to present a summary of the invention to briefly indicate the nature and substance of the invention. It is submitted with the understanding that it will not be used to interpret or limit the scope or meaning of the claims.

Embodiments of the invention relate to compositions comprising adult bone marrow derived precursors of mesenchymal stem cells. These cells are administered in vivo, such as for example, the heart and regenerate the myocardium.

In a preferred embodiment, a method of preventing or treating cardiovascular diseases or disorders comprises isolating CD271$^+$ mesenchymal stem cell precursors (MSCs) from bone marrow of a subject; administering to a patient a therapeutically effective amount of isolated. CD271$^+$ mesenchymal stem cell (MSC) precursors.

In one embodiment, the CD271$^+$ MSCs are isolated from bone marrow cells having a low affinity nerve growth receptor (NGFR; CD271). The CD271$^+$ stem cells are isolated from donors (or sources) comprising: autologous, syngeneic, allogeneic, or xenogeneic. The MSC precursor cells differentiate into at least one lineage comprising: myocardial, vascular, or endothelial lineages.

In another embodiment, the isolated precursor mesenchymal stem cells are cultured ex vivo and expanded prior to administration to a patient. In one embodiment, the non-adherent stem cells are expanded and administered to a patient. In another embodiment, the precursor mesenchymal stem cells are optionally administered to a patient in varying concentrations over a period of time. In one embodiment, the wherein the precursor mesenchymal stem cells are optionally conditioned with media conditioned by heart derived stromal cells.

In another embodiment, one or more agents are optionally administered to the patient, the agents comprising at least one of: cytokines, chemotactic factors, growth factors, or differentiation factors.

In a preferred embodiment, an adult stem cell comprises a bone marrow mesenchymal stem cell (MSC) precursor derived cell having a CD271$^+$ phenotype.

Other aspects are described it infra.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9A shows a slice from Border zone with positive cells embedded in vascular wall and also between host myocytes.

FIG. 9B shows a remote zone towards the base of the heart still showing injected human cells.

FIG. 9C shows a large blood vessel with alu positive cells in remote area.

FIG. 9D shows the border zone of another heart with numerous positive cells.

DETAILED DESCRIPTION

Figure 1:
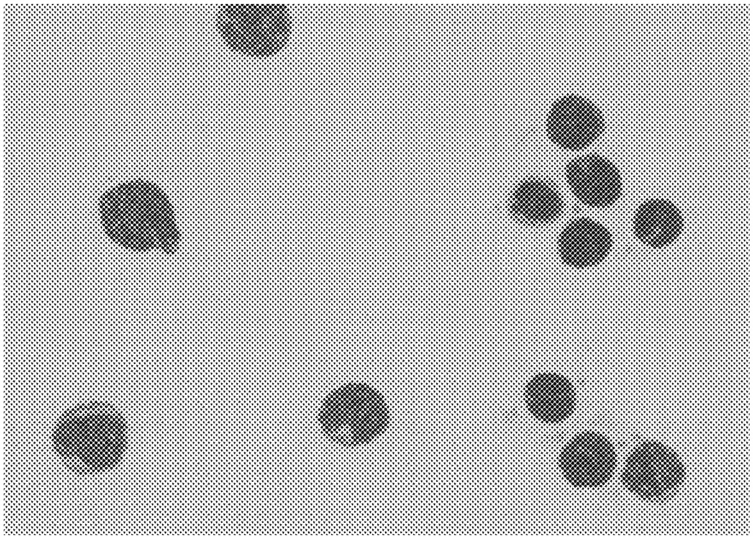
FIG. 1 shows the morphology of CD271$^+$ cells. Cytospins were prepared and stained with Wright Giemsa.

Stem cells show potential for many different areas of health and medical research. Some of the most serious medical conditions, such as cancer and birth defects, are caused by problems that occur somewhere in the process of stem cell differentiation or maintenance. Broadly, there are two different types of stem cells, embryonic stem cells and adult stem cells. Embryonic stem cells are found in blastocysts and have the ability to differentiate into all of the specialized embryonic tissues. Adult stem cells are undifferentiated cells found throughout the body after embryonic development. Adult stem cells are able to divide and replenish dying cells and regenerate damaged tissue. Furthermore, adult stem cells can maintain the normal turnover of regenerative organs such as blood, skin and intestinal tissue. Adult stem cells have the ability to divide and self-renew indefinitely and are able to generate all of the cell types of the organ from which they originate.

Stem cells can be classified as being totipotent, pluripotent, multipotent or unipotent based on their potential to differentiate into different cell types. Totipotent stem cells are produced from the fusion of gametes and the first few divisions of the fertilized egg. These cells can differentiate into embryonic and extra-embryonic cell types. Pluripotent stem cells can differentiate into cells from any of the three germ layers. Multipotent calls can produce only cells of a closely related family. Unipotent cells can produce only one cell type, but have the property of self-renewal which distinguishes them from non-stem cells. Most adult stem cells are lineage restricted multipotent stem cells, and are referred to by their tissue of origin. Pluripotent adult stem cells are rare and generally small in number but can be found in a number of tissues including umbilical cord blood (Ratajczak M. Z., et al., *Leukemia* 21(5): 860-867 (2007)). There are several different types of adult stem cells including, but not limited to, adipose derived stem cells (Zuk, P. A. et al., *Tissue Engineering* 7: 211-216) (2000), epithelial stem cells, hematopoietic stem cells, mammary stem cells (Shackleton, M., et al., *Breast Cancer* R E. 7: 86-95 (2005)), mesenchymal stem cells, endothelial stem cells, neural stem cells (Alvarez-Bullta, A., et al., *Brain Res. Bull.* 57: 751-758 (2002)), olfactory stem cells (Murrel. W., et al., *Dev. Dyn.* 233: 496-515 (2005)), testicular stem cells, dental pulp derived stem cells, and umbilical cord blood hematopoietic progenitor cells.

When an adult stem cell divides, it creates another cell like itself and a cell more differentiated than itself. This process of asymmetric cell division, gives rise to one identical daughter cell and one early transient-amplifying cell (early TA), which possesses high proliferative capacity. Through a series of cell divisions, the early TA cell gives rise to a late TA cell followed by a tissue-specific progenitor cell and finally to the bulk of differentiated cells that make up the organ or tissue (Ribacka, C., et al. *Ann. Med.* epub ahead of print: 1-10 (2008)).

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Embodiments of the invention may be practiced without the theoretical aspects presented. Moreover, the theoretical aspects are presented with the understanding that Applicants do not seek to be bound by the theory presented.

Definitions

The terminology used herein is for the purpose of describing particular embodiments only and is not intended to be limiting of the invention. As used herein, the singular forms “a”, “an” and “the” are intended to include the plural forms as well, unless the context clearly indicates otherwise. Furthermore, to the extent that the terms “including”, “includes”, “having”, “has”, “with”, or variants thereof are used in either the detailed description and/or the claims, such terms are intended to be inclusive in a manner similar to the term “comprising.”

The term “about” or “approximately” means within an acceptable error range for the particular value as determined by one of ordinary skill in the art, which will depend in part on how the value is measured or determined, i.e., the limitations of the measurement system. For example, “about” can mean within 1 or more than 1 standard deviation, per the practice in the art. Alternatively, “about” can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term “about” meaning within an acceptable error range for the particular value should be assumed.

A “stem cell” as used herein is an undifferentiated cell which is capable of essentially unlimited propagation either in vivo or ex vivo and capable of differentiation to other cell types. This can be to certain differentiated, committed, immature, progenitor, or mature cell types present in the tissue from which it was isolated, or dramatically differentiated cell types, such as for example the erythrocytes and lymphocytes that derive from a common precursor cell, or even to cell types at any stage in a tissue completely different from the tissue from which the stem cell is obtained. For example, blood stem cells may become brain cells or liver cells, neural stem cells can become blood cells, such that stem cells are pluripotential, and given the appropriate signals from their environment, they can differentiate into any tissue in the body.

"Propagation" can be determined, for example, by the ability of an isolated stem cell to be propagated through at least 50, preferably 100, and even up to 200 or more cell divisions in a cell culture system. Stem cells can be "totipotent," meaning that they can give rise to all the cells of an organism as for germ cells. Stem cells can also be "pluripotent," meaning that they can give rise to many different cell types, but not all the cells of an organism. When a stem cell differentiates it generally gives rise to a more adult cell type, which may be a partially differentiated cell such as a progenitor cell, a differentiated cell, or a terminally differentiated cell. Stem cells can be highly motile.

"Isolating" a stem cell refers to the process of removing a stem cell from a tissue sample and separating away other cells which are not stem cells of the tissue. An isolated stem cell will be generally free from contamination by other cell types, i.e. "homogeneity" or purity" and will generally have the capability of propagation and differentiation to produce mature cells of the tissue from which it was isolated. An isolated stem cell can exist in the presence of a small fraction of other cell types which do not interfere with the utilization of the stem cell for analysis or production of other, differentiated cell types. Isolated stem cells will generally be at least 30%, 40%, 50%, 60%, 70%, 80%, 85%, 90%, 95%, 98%, 99%, or 99.9% pure. Preferably, isolated stem cells according to the invention will be at least 98% or at least 99% pure.

As used herein, "culturing" refers to propagating or nurturing a cell, collection of cells, tissue, or organ, by incubating for a period of time in an environment and under conditions which support cell viability or propagation. Culturing can include one or more of the steps of expanding and proliferating a cell, collection of cells, tissue, or organ according to the invention.

"Bone marrow derived progenitor cell" (BMDC) or "bone marrow derived stem cell" refers to a primitive stem cell with the machinery for self-renewal constitutively active. Included in this definition are stem cells that are totipotent, pluripotent and precursors. A "precursor cell" can be any cell in a cell differentiation pathway that is capable of differentiating into a more mature cell. As such, the term "precursor cell population" refers to a group of cells capable of developing into a more mature cell. A precursor cell population can comprise cells that are totipotent, cells that are pluripotent and cells that are stem cell lineage restricted (i.e. cells capable of developing into less than all hematopoietic lineages, or into, for example, only cells of erythroid lineage).

As used herein, the term "autologous" is meant to refer to any material derived from the same individual to whom it is later to be re-introduced into the individual.

The term "xenogeneic cell" refers to a cell that derives from a different animal species than the animal species that becomes the recipient animal host in a transplantation or vaccination procedure.

The term "allogeneic cell" refers to a cell that is of the same animal species but genetically different in one or more genetic loci as the animal that becomes the "recipient host". This usually applies to cells transplanted from one animal to another non-identical animal of the same species.

The term "syngeneic cell" refers to a cell which is of the same animal species and has the same genetic composition for most genotypic and phenotypic markers as the animal who becomes the recipient host of that cell line in a transplantation or vaccination procedure. This usually applies to cells transplanted from identical twins or may be applied to cells transplanted between highly inbred animals.

As used herein, the term "safe and effective amount" or "therapeutic amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

"Patient" or "subject" refers to mammals and includes human and veterinary subjects.

As used herein the phrase "diagnosing" refers to classifying a disease or a symptom, determining a severity of the disease, monitoring disease progression, forecasting an outcome of a disease and/or prospects of recovery. The term "detecting" may also optionally encompass any of the above. It should be noted that a "biological sample obtained from the subject" may also optionally comprise a sample that has not been physically removed from the subject, as described in greater detail below.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. As used herein, "ameliorated" or "treatment" refers to a symptom which is approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests.

As defined herein, "a therapeutically effective amount" of an agent or compound, cells etc., (i.e., an effective dosage) means an amount sufficient to produce a therapeutically (e.g., clinically) desirable result. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments. A "prophylactically effective amount" may refer to the amount of precursor mesenchymal stem cells sufficient to prevent the recurrence of heart diseases or disorders, for example, ischemia, or the occurrence of such in a patient, including but not limited to those predisposed to heart disease, for example those genetically predisposed to heart disease, stroke, etc. A prophylactically effective amount may also refer to the amount of the prophylactic agent that provides a prophylactic benefit in the prevention of disease.

The term “sample” is meant to be interpreted in its broadest sense. A “sample” refers to a biological sample, such as, for example; one or more cells, tissues, or fluids (including, without limitation, plasma, serum, whole blood, cerebrospinal fluid, lymph, tears, urine, saliva, milk, pus, and tissue exudates and secretions) isolated from an individual or from cell culture constituents, as well as samples obtained from, for example, a laboratory procedure. A biological sample may comprise chromosomes isolated from cells (e.g., a spread of metaphase chromosomes), organelles or membranes isolated from cells, whole cells or tissues, nucleic acid such as genomic DNA in solution or bound to a solid support such as for Southern analysis, RNA in solution or bound to a solid support such as for Northern analysis, cDNA in solution or bound to a solid support, oligonucleotides in solution or bound to a solid support, polypeptides or peptides in solution or bound to a solid support, a tissue, a tissue print and the like.

Numerous well known tissue or fluid collection methods can be utilized to collect the biological sample from the subject in order to determine the level of DNA, RNA and/or polypeptide of the variant of interest in the subject. Examples include, but are not limited to, fine needle biopsy, needle biopsy, core needle biopsy and surgical biopsy e.g., brain biopsy), and lavage. Regardless of the procedure employed, once a biopsy/sample is obtained the level of the variant can be determined and a diagnosis can thus be made.

As used herein, “heart disease or disorders” or “cardiovascular diseases or disorders” refer to any type of heart disease or disorders including cardiomyopathy, hypertrophic cardiomyopathy, dilated cardiomyopathy, atherosclerosis, coronary a e disease, ischemic heart disease, myocarditis, viral infection, wounds, hypertensive heart disease, valvular disease, congenital heart disease, myocardial infarction, congestive heart failure, arrhythmias, diseases resulting in remodeling of the heart, heart failure, ischemia, myocardial infarction, transplantation, hypertension, restenosis, angina pectoris, rheumatic heart disease, or congenital cardiovascular defects. Diseases or disorders of the heart can be due to any reason, such as for example, damage to cardiac tissue s as a loss of contractility (e.g., as might be demonstrated by a decreased ejection fraction).

Cardiac damage or disorders characterized by insufficient cardiac function includes any impairment or absence of a normal cardiac function or presence of an abnormal cardiac function. Abnormal cardiac function can be the result of disease, injury, and/or aging. As used herein, abnormal cardiac function includes morphological and/or functional abnormality of a cardiomyocyte, a population of cardiomyocytes, or the heart itself. Non-limiting examples of morphological and functional abnormalities include physical deterioration and/or death of cardiomyocytes, abnormal growth patterns of cardiomyocytes, abnormalities in the physical connection between cardiomyocytes, under- or over-production of a substance or substances by cardiomyocytes, failure of cardiomyocytes to produce a substance or substances which they normally produce, and transmission of electrical impulses in abnormal patterns or at abnormal times. Abnormalities at a more gross level include dyskinesis, reduced rejection fraction, changes as Observed by echocardiography (e.g., dilatation), changes in EKG, changes in exercise tolerance, reduced capillary perfusion, and changes as observed by angiography. Abnormal cardiac function is seen with many disorders including, for example, ischemic heart disease, e.g., angina pectoris, myocardial infarction, chronic ischemic heart disease, hypertensive heart disease, pulmonary heart disease (cor pulmonale), valvular heart disease, e.g., rheumatic fever, mitral valve prolapse, calcification of mitral annulus, carcinoid heart disease, infective endocarditis, congenital heart disease, myocardial disease, e.g., myocarditis, dilated cardiomyopathy, hypertensive cardiomyopathy, cardiac disorders which result in congestive heart failure, and tumors of the heart, e.g., primary sarcomas and secondary tumors. Heart damage also includes wounds, such as for example, knife wound; biological (e.g. viral; autoimmune diseases) or chemical (e.g. chemotherapy, drugs); surgery; transplantation and the like.

“Myocardial ischemia” refers to a lack of oxygen flow to the heart which results in myocardial ischemic damage. As used herein, the phrase myocardial ischemic damage includes damage caused by reduced blood flow to the myocardium. Non-limiting examples of causes of myocardial ischemia and myocardial ischemic damage include: decreased aortic diastolic pressure, increased intraventricular pressure and myocardial contraction, coronary artery stenosis (e.g., coronary ligation, fixed coronary stenosis, acute plaque change (e.g., rupture, hemorrhage), coronary artery thrombosis, vasoconstriction), aortic valve stenosis and regurgitation, and increased right atrial pressure. Non-limiting examples of adverse effects of myocardial ischemia and myocardial ischemic damage include: myocyte damage (myocyte cell loss, myocyte hypertrophy, myocyte cellular hyperplasia), angina. (e.g., stable angina, variant angina, unstable angina, sudden cardiac death), myocardial infarction, and congestive heart failure. Damage due to myocardial ischemia may be acute or chronic, and consequences may include scar formation, cardiac remodeling, cardiac hypertrophy, wall thinning, dilatation, and associated functional changes. The existence and etiology of acute or chronic myocardial damage and/or myocardial ischemia may be diagnosed using any of a variety of methods and techniques well known in the art including, e.g., non-invasive imaging (e.g., MRI, echocardiography), angiography, stress testing, assays for cardiac-specific proteins such as cardiac troponin, and clinical symptoms. These methods and techniques as well as other appropriate techniques may be used to determine which subjects are suitable candidates for the treatment methods described herein.

Bone Marrow Derived CD271$^+$ Cells

Ischemic cardiomyopathy is the leading cause of heart failure in developed countries, few therapies exist to improve cardiac function once infarct remodeling has occurred, and treatments that actually reverse deleterious remodeling of the heart after a myocardial infarction (MI) are lacking. Administration of adult bone marrow derived progenitor cells into the heart holds promise to regenerate myocardium. The inventors have demonstrated in preclinical models (and for the first time in humans in preliminary data) the ability of bone marrow (BM) derived mesenchymal stem cells (MSCs) delivered to the heart via surgical and catheter delivery systems to engraft, support reverse remodeling, improve cardiac function, and reduce scar size. While MSCs have shown great promise, these cells require 4 to 5 weeks of culture to obtain sufficient quantities to be injected. A precursor of MSCs, can be isolated from the bone marrow based upon expression of the low affinity nerve growth factor receptor (NGFR; CD271) and the CD271$^+$ cells are a readily available cell source for therapeutic use. Importantly, bone marrow derived CD271$^+$ cells can be obtained from a bone marrow aspiration and isolated to sufficient quantities in 4 to 5 hours, providing a logistical advantage for immediate use. Moreover, these cells are dramatically superior in efficacy to cultured MSCs. The goal of the studies is to conduct preclinical trials testing BM-CD271$^+$ cells in a rodent and swine model of myocardial infarction and translate this work to a clinical trial of direct surgical injections of CD-271$^+$ cells following coronary artery bypass surgery. Without wishing to be bound by theory, the central hypothesis is that BM-CD271$^+$ cells delivered by surgical injection will engraft, improve cardiac function, and reduce scar size.

Cellular therapy for chronic ischemic cardiomyopathy offers the potential to prevent further tissue damage which would lead to heart failure. The inventors have demonstrated that human CD271$^+$ cells are indeed precursors of MSC and have the potential to repair ischemic tissue in a mouse model of myocardial infarction (MI). CD271$^+$ cells are more potent and have greater capacity for differentiation into cardiomyocytes than do cultured MSCs. Importantly, adequate numbers of CD271$^+$ cells can be isolated from BM in four to five hours providing a major logistic advance to treat patients immediately with autologous bone marrow derived therapy.

In a preferred embodiment, bone marrow derived (BM) derived precursor mesenchymal stem CD271$^+$ cells are utilized in the treatment of ischemic tissue in patients with heart failure.

In another preferred embodiment, a method of preventing or treating cardiovascular diseases or disorders comprises administering to a patient an effective amount of CD271$^+$ stem cells. Preferably, the CD271$^+$ cells are isolated from bone marrow cells having a low affinity nerve growth receptor (NOR; CD271).

In another preferred embodiment, the CD271$^+$ stem cells are autologous, syngeneic, allogeneic, xenogeneic or combinations thereof. The administered stem cells populate and repair damaged tissue, for example, cardiac tissue. These cells differentiate into the various lineages resulting in the regeneration and repair of damaged tissue.

In another preferred embodiment, one or more agents are optionally administered to the patient, the agents comprising at least one of: cytokines, chemotactic factors, growth factors, or differentiation factors.

In one aspect, provided herein are methods for treating a patient with a heart disease or injury comprising administering a therapeutic cell composition to a patient with a disease or injury of the heart or circulatory system, and evaluating the patient for improvements in cardiac function, wherein said cell composition comprises CD271$^+$ as described herein one embodiment, the heart disease is a cardiomyopathy. In specific embodiments, the cardiomyopathy is either idiopathic or a cardiomyopathy with a known cause. In other embodiments, the cardiomyopathy is either ischemic or nonischemic in nature. In another embodiments, the disease of the heart or circulatory system comprises one or more of angioplasty, aneurysm, angina (angina pectoris), aortic stenosis, aortitis, arrhythmias, arteriosclerosis, arteritis, asymmetric septal hypertrophy (ASH), atherosclerosis, atrial fibrillation and flutter, bacterial endocarditis, Barlow's Syndrome (mitral valve prolapse), bradycardia, Buerger's Disease (thromboangiitis obliterans), cardiomegaly, cardiomyopathy, carditis, carotid artery disease, coarctation of the aorta, congenital heart diseases (congenital heart defects), congestive heart failure (heart failure), coronary artery disease, Eisenmenger's Syndrome, embolism, endocarditis, erythromelalgia, fibrillation, fibromuscular dysplasia, heart block, heart murmur, hypertension, hypotension, idiopathic infantile arterial calcification, Kawasaki Disease (mucocutaneous lymph node syndrome, mucocutaneous lymph node disease, infantile polyarteritis), metabolic syndrome, microvascular angina, myocardial infarction (heart attacks), myocarditis, paroxysmal atrial tachycardia (PAT), periarteritis nodosa (potyarteritis, polyarteritis nodosa), pericarditis, peripheral vascular disease, critical limb ischemia, diabetic vasculopathy, phlebitis, pulmonary valve stenosis (pulmonic stenosis), Raynaud's Disease, renal artery stenosis, renovascular hypertension, rheumatic heart disease, septal defects, silent ischemia, syndrome X, tachycardia, Takayasu's Arteritis, Tetralogy of Fallot, transposition of the great vessels, tricuspid atresia, truncus arteriosus, valvular heart disease, varicose ulcers, varicose veins, vasculitis, ventricular septal defect, Wolff-Parkinson-White Syndrome, or endocardial cushion defect.

In other embodiments, the disease of the heart or circulatory system comprises one or more of acute rheumatic fever, acute rheumatic pericarditis, acute rheumatic endocarditis, acute rheumatic myocarditis, chronic rheumatic heart diseases, diseases of the mitral valve, mitral stenosis, rheumatic mitral insufficiency, diseases of aortic valve, diseases of other endocardial structures, ischemic heart disease (acute and subacute), angina pectoris, diseases of pulmonary circulation (acute pulmonary heart disease, pulmonary embolism, chronic pulmonary heart disease), kyphoscoliotic heart disease, myocarditis, endocarditis, endomyocardial fibrosis, endocardial fibroelastosis, atrioventricular block, cardiac dysrhythmias, myocardial degeneration, diseases of the circulatory system including cerebrovascular disease, occlusion and stenosis of precerebral arteries, occlusion of cerebral arteries, diseases of arteries, arterioles and capillaries (atherosclerosis, aneurysm), or diseases of veins and lymphatic vessels.

In one embodiment, treatment comprises treatment of a patient with a cardiomyopathy with a therapeutic cell composition comprising CD271$^+$ cells, either with or without another cell type. In other preferred embodiments, the patient experiences benefits from the therapy, for example from the ability of the cells to support the growth of other cells, including stem cells or progenitor cells present in the heart, from the tissue ingrowth or vascularization of the tissue, and from the presence of beneficial cellular factors, chemokines, cytokines and the like.

Improvement in an individual having a disease or disorder of the circulatory system, wherein the individual is administered the CD271$^+$ cells or therapeutic compositions provided herein, can be assessed or demonstrated by detectable improvement in one or more symptoms of the disease or disorder of the circulatory system.

In another embodiment, improvement in an individual having a disease or disorder of the circulatory system, wherein the individual is administered the CD271$^+$ cells or therapeutic compositions provided herein, can be assessed or demonstrated by detectable improvement in one or more, indicia of cardiac function, for example, demonstration of detectable improvement in one or more of chest cardiac output (CO), cardiac index (CI), pulmonary artery wedge pressures (PAWP), and cardiac index (CI), % fractional shortening (% FS), ejection fraction (EF), left ventricular ejection fraction (LVEF); left ventricular end diastolic diameter (LVEDD), left ventricular end systolic diameter (LVESD), contractility (e.g. dP/dt), pressure-volume loops, measurements of cardiac work, an increase in atrial or ventricular functioning; an increase in pumping efficiency, a decrease in the rate of loss of pumping efficiency, a decrease in loss of hemodynamic functioning; and a decrease in complications associated with cardiomyopathy, as compared to the individual prior to administration of CD271$^+$ cells.

Improvement in an individual receiving the therapeutic compositions provided herein can also be assessed by subjective metrics, e.g., the individual's self-assessment about his or her state of health following administration.

In certain embodiments, the methods of treatment provided herein comprise inducing the therapeutic CD271$^+$ cells to differentiate along mesenchymal lineage, e.g., towards a cardiomyogenic, angiogenic or vasculogenic phenotype, or into cells such as myocytes, cardiomyocytes, endothelial cells, myocardial cells, epicardial cells, vascular endothelial cells, smooth muscle cells (e.g. vascular smooth muscle cells).

Administration of CD271$^+$ cells, or therapeutic compositions comprising such cells, to an individual in need thereof, can be accomplished, e.g., by transplantation, implantation (e.g., of the cells themselves or the cells as part of a matrix-cell combination), injection (e.g., directly to the site of the disease or condition, for example, directly to an ischemic site in the heart of an individual who has had a myocardial infarction), infusion, delivery via catheter, or any other means known in the art for providing cell therapy.

In one embodiment, the therapeutic cell compositions are provided to an individual in need thereof, for example, by injection into one or more sites in the individual. In a specific embodiment, the therapeutic cell compositions are provided by intracardiac injection, e.g., to an ischemic area in the heart. In other specific embodiments, the cells are injected onto the surface of the heart, into an adjacent area, or even to a more remote area. In preferred embodiments, the cells can home to the diseased or injured area.

An individual having a disease or condition of the coronary or vascular systems can be administered CD271$^+$ cells at any time the cells would be therapeutically beneficial. In certain embodiments, for example, the cells or therapeutic compositions of the invention are administered within 1, 2, 3, 4, 5, 6, 7, 8, 9, 10, 11, 12, 13, 14, 15, 16, 17, 18, 19, 20, 21, 22, or 24 hours, or 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days of the myocardial infarction. Administration proximal in time to a myocardial infarction, e.g., within 1-3 or 1-7 days, is preferable to administration distal in time, e.g., after 3 or 7 days after a myocardial infarction. In other embodiments, the cells or therapeutic compositions of the invention are administered within 1, 2, 3, 4, 5, 6, 7, 8, 9, 10, 11, 12, 13, 14, 15, 16, 17, 18, 19, 20, 21, 22, 23, or 24 hours, or 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days of initial diagnosis of the disease or condition.

Also provided herein are kits for use in the treatment of myocardial infarction. The kits provide the therapeutic cell composition which can be prepared in a pharmaceutically acceptable form, for example by mixing with a pharmaceutically acceptable carrier, and an applicator, along with instructions for use. Ideally the kit can be used in the field, for example in a physician's office, or by an emergency care provider to be applied to a patient diagnosed as having had a myocardial infarction or similar cardiac event.

In some aspects of the methods of treatment provided herein, the CD271$^+$ cells are administered with stem cells that are not CD271$^+$ cells, myoblasts, myocytes, cardiomyoblasts, cardiomyocytes, or progenitors of myoblasts, myocytes, cardiomyoblasts, and/or cardiomyocytes.

In a specific embodiment, the methods of treatment provided herein comprise administering CD271$^+$ cells, e.g., a therapeutic composition comprising the cells, to a patient with a disease of the heart or circulatory system; and evaluating the patient for improvements in cardiac function, wherein the therapeutic cell composition is administered as a matrix-cell complex. In certain embodiments, the matrix is a scaffold, preferably bioabsorbable, comprising at least the cells.

In some embodiments, populations of CD271$^+$ cells are incubated or are administered to a patient in the presence of one or more factors which stimulate stem or progenitor cell differentiation along a cardiogenic, angiogenic, hemangiogenic, or vasculogenic pathway. Such factors are known in the art; determination of suitable conditions for differentiation can be accomplished with routine experimentation. Such factors include, but are not limited to factors, such as growth factors, chemokines, cytokines, cellular products, demethylating agents, and other stimuli which are now known or later determined to stimulate differentiation, for example of stem cells, along cardiogenic, angiogenic, hemangiogenic, or vasculogenic pathways or lineages. For example, CD271$^+$ cells may be differentiated along cardiogenic, angiogenic, hemangiogenic, or vasculogenic pathways or lineages by culture of the cells in the presence of factors comprising at least one of a demethylation agent, a BMP, FGF, Wnt factor protein, Hedgehog, and/or anti-Wnt factors.

Inclusion of demethylation agents tends to allow the cells to differentiate along mesenchymal lines, toward a cardiomyogenic pathway. Differentiation can be determined by, for example, expression of at least one of cardiomyosin, skeletal myosin, or GATA4; or by the acquisition of a beating rhythm, spontaneous or otherwise induced; or by the ability to integrate at least partially into a patient's cardiac muscle without inducing arrhythmias. Demethylation agents that can be used to initiate such differentiation include, but are not limited to, 5-azacytidine, 5-aza-2'-deoxycytidine, dimethylsulfoxide, chelerythrine chloride, retinoic acid or salts thereof, 2-amino-4-(ethylthio)butyric acid, procainamide, and procaine.

In certain embodiments herein, cells become cardiomyogenic, angiogenic, hemangiogenic, or vasculogenic cells, or progenitors. Preferably cells integrate into a recipient's cardiovascular system including but not limited to heart muscle, vascular and other structures of the heart, cardiac or peripheral blood vessels, and the like. In certain other embodiments, the CD271$^+$ cells differentiate into cells acquiring two or more of the indicia of cardiomyogenic cells or their progenitors, and able to integrate into a recipient's heart or vasculature. In specific embodiments, the cells, which administered to an individual, result in no increase in arrhythmias, heart defects, blood vessel defects or other anomalies of the individual's circulatory system or health. In certain embodiments, the CD271$^+$ cells act to promote the differentiation of stem cells naturally present in the patient's cardiac muscle, blood vessels, blood and the like to themselves differentiate into for example, cardiomyocytes, or at least along cardiomyogenic, angiogenic, hemangiogenic, or vasculogenic lines.

CD271$^+$ cells, and populations of such cells, can be provided therapeutically or prophylactically to an individual, e.g., an individual having a disease, disorder or condition of, or affecting, the heart or circulatory system. Such diseases, disorders or conditions can include congestive heart failure due to atherosclerosis, cardiomyopathy, or cardiac injury, e.g., an ischemic injury, such as from myocardial infarction or wound (acute or chronic).

The CD271$^+$ cells may be administered to an individual in the form of a therapeutic composition comprising the cells and another therapeutic agent, such as insulin-like growth factor (TGF), platelet-derived growth factor (PDGF), epidemlal growth factor (EGF), fibroblast growth factor (FGF), vascular endothelial growth factor (VEGF), hepatocyte growth factor (HGF), IL-8, an antithrombogenic agent (e.g., heparin, heparin derivatives, urokinase, and PPack (dextrophenylalanine proline arginine chloromethylketone); antithrombin compounds, platelet receptor antagonists, anti-thrombin antibodies, anti-platelet receptor antibodies, aspirin, dipyridamole, protamine, hirudin, prostaglandin inhibitors, and/or platelet inhibitors), an antiapoptotic agent (e.g., EPO, EPO derivatives and analogs, and their salts, TPO, IGF-I IGF-II, hepatocyte growth factor (HGF), or caspase inhibitors), an anti-inflammatory agent (e.g., P38 MAP kinase inhibitors, statins, IL-6 and IL-1 inhibitors, Pemirolast, Tranilast, Remicade, Sirolimus, nonsteroidal anti-inflammatory compounds, for example, acetylsalicylic acid, ibuprofen, Tepoxalin, Tolmetin, or Suprofen), an immunosuppressive or immunomodulatory agent (e.g., calcineurin inhibitors, for example cyclosporine, Tacrolimus, mTOR inhibitors such as Sirolimus or Everolimus; anti-proliferatives such as azathioprine and mycophenolate mofetil; corticosteroids, e.g., prednisolone or hydrocortisone; antibodies such as monoclonal anti-IL-2Ra receptor antibodies, Basiliximab, Daclizuma, polyclonal anti-T-cell antibodies such as anti-thymocyte globulin (ATG), anti-lymphocyte globulin (ALG), and the monoclonal anti-T cell antibody OKT3, and/or an antioxidant (e.g., probucol; vitamins A, C, and E, coenzyme Q-10, glutathione, L cysteine, N-acetylcysteine, or antioxidant derivative, analogs or salts of the foregoing). In certain embodiments, therapeutic compositions comprising the $CD271^+$ cells further comprise one or more additional cell types, e.g., adult cells (for example, fibroblasts or endodermal cells), or stem or progenitor cells. Such therapeutic agents and/or one or more additional cells can be administered to an individual in need thereof individually or in combinations or two or more such compounds or agents.

In certain embodiments, the individual to be treated is a mammal. In a specific embodiment the individual to be treated is a human. In specific embodiments, the individual is a livestock animal or a domestic animal. In other specific embodiments, the individual to be treated is a horse, sheep, cow or steer, pig, dog or cat.

In another preferred embodiment, the population of stem cells is at least about 80% pure as compared to a control sample of cells isolated from a heart tissue, preferably, the stem cell population is about 90% pure as compared to a control sample of cells, preferably, the stem cell population is about 95%, 96%, 97%, 98%, 99%, 99.9% pure as compared to a control sample of cells.

In another preferred embodiment, the isolated $CD271^+$ stem cell populations can be used in any assay desired by the end user, such as for example, expressing a non-native or foreign molecule, a native molecule which may or may not be activated in the cells. Examples of such molecules can be growth factors, receptors, ligands, therapeutic agents, etc. The molecules can be selected by the end user for expression by the isolated stem cells depending on the end user's need. The molecules comprise, for example, a polypeptide, a peptide, an oligonucleotide, a polynucleotide, an organic or inorganic molecule.

In another preferred embodiment, stem cells may be embryonic stem cells, adult stem cells, umbilical cord blood stem cells, somatic stem cells or cancer stem cells. In preferred embodiments, the stem cells are adult stem cells, preferably cardiac stem cells.

Additionally, the stem cells of the current invention may be hematopoietic stem cells, or mesenchymal stem cells. The stem cells of the current invention may be totipotent, pluripotent, multipotent or unipotent stem cells. Stem cells according to the current invention may be selected for by the presence of one or more stem cell markers including but not limited to: CD133, CD34, CD38, CD117/c-kit, OCT3/4, Nanog, RUNX2, SOX9, Integrin, SPARC, osteocalcin, endoglin and STRO-1.

The stem cells of the current invention may be primary stem cells or may be derived from an established stem cell line, premalignant stem cell line, cancer cell line, or any cell line that manifests any stem cell marker. Primary stem cells may be derived from a cancer patient or a healthy patient.

Administration: Isolation of $CD271^+$ stem cell populations is useful many types of applications, for example, transplantation into heart or other organs for the treatment of cardiac diseases or disorders, such as damaged myocardium. As used herein "damaged myocardium" refers to myocardial cells which have been exposed to ischemic conditions. These ischemic conditions may be caused by a myocardial infarction, or other cardiovascular disease or related complaint. The lack of oxygen causes the death of the cells in the surrounding area, leaving an infarct, which will eventually scar. As used herein "age-related cardiomyopathy" refers to the deterioration of the myocardium as a result of intrinsic mechanisms occurring as the organism ages.

In a preferred embodiment, the stem cells are used in methods of repairing and/or regenerating damaged myocardium or age-related cardiomyopathy in a subject in need thereof by administering isolated stem cells to areas of damaged myocardium, wherein the administered stem cells differentiate into one or more of myocytes, endothelial cells, or smooth muscle cells. The differentiated cells may proliferate and form various cardiac structures including coronary arteries, arterioles, capillaries, and myocardium, which are all structures essential for proper function in the heart. The ability to restore both functional and structural integrity is yet another aspect of this invention. In a preferred embodiment, the stem cells are adult cardiac stem cells. In another embodiment, adult cardiac stem cells are isolated from cardiac tissue harvested from the subject in need of therapeutic treatment for one of the cardiac or vasculature conditions and implanted back into the subject.

In another preferred embodiment, the isolated $CD271^+$ stem cells are cultured and expanded ex vivo prior to administration of the stem cells to a patient. The cells can be for example, autologous, syngeneic, allogeneic, xenogeneic or any combination thereof. The same source of stem cells does not have to be used if successive administrations are required.

Thus, in preferred embodiments, the invention involves administering a therapeutically effective dose or amount of stem cells to the heart. An effective dose is an amount sufficient to effect a beneficial or desired clinical result. The dose could be administered in one or more administrations. The precise determination of what would be considered an effective dose may be based on factors individual to each patient, including their size, age, area of myocardial damage, and amount of time since damage. One skilled in the art, specifically a physician or cardiologist, would be able to determine the number of stem cells that would constitute an effective dose without undue experimentation.

In some embodiments of the invention, the isolated stem cells are activated prior to administration to a subject. Activation of the stein cells may be accomplished by exposing the isolated stem cells to one or more cytokines, such as hepatocyte growth factor (HGF), insulin-like growth factor-I (IGF-1), or variant thereof. HGF positively influences stem cell migration and homing through the activation of the c-Met receptor (Kollet et al. (2003) *J. Clin. Invest.* 112: 160-169; Linke et al. (2005) *Proc. Natl. Acad. Sci. USA* 102: 8966-8971; Rosu-Myles et al. (2005) *J Cell. Sci.* 118:

4343-4352; Urbanek et al. (2005) *Circ. Res.* 97: 663-673). Similarly, IGF-1 and its corresponding receptor (IGF-1R) induce cardiac stem cell division, upregulate telomerase activity, hinder replicative senescence and preserve the pool of functionally-competent cardiac stem cells in the heart (Kajstura et al. (2001) *Diabetes* 50: 1414-1424; Torella et al. (2004) *Circ. Res.* 94: 514-524; Davis et al. (2006) *Proc. Natl. Acad. Sci. USA* 103: 8155-8160). In a preferred embodiment, the isolated stem cells are contacted with hepatocyte growth factor (HGF) and/or insulin-like growth factor-I (IGF-1).

Some other non-limiting examples of cytokines that are suitable for the activation of the isolated stem cells include Activin A, Bone Morphogenic Protein 2, Bone Morphogenic Protein 4, Bone Morphogenic Protein 6, Cardiotrophin-1, Fibroblast Growth Factor 1, Fibroblast Growth Factor 4, Flt3 Ligand, Glial-Derived Neurotrophic Factor, Heparin, Insulin-like Growth Factor-II, Insulin-Like Growth Factor Binding Protein-3, Insulin-Like Growth Factor Binding Protein-5, Interleukin-3, Interleukin-6, Interleukin-8, Leukemia Inhibitory Factor, Midkine, Platelet-Derived Growth Factor AA, Platelet-Derived Growth Factor BB, Progesterone, Putrescine, Stem Cell Factor, Stromal-Derived Factor-I, Thrombopoietin, Transforming Growth Factor-$\alpha$, Transforming Growth Factor-$\beta$1, Transforming Growth Factor-P2, Transforming Growth Factor-$\beta$3, Vascular Endothelial Growth Factor, Wnt1, Wnt3a, and Wnt5a, as described in Kanemura et al. (2005) *Cell Transplant.* 14: 673-682; Kaplan et al. (2005) *Nature* 438: 750-751; Xu et al. (2005) *Methods Mol. Med.* 121: 189-202; Quinn et al. (2005) *Methods Mol. Med.* 121: 125-148; Almeida et al. (2005) *J Biol. Chem.* 280: 41342-41351; Barnabe-Heider et al (2005) *Neuron* 48: 253-265; Madlambayan et al. (2005) *Exp Hematol* 33: 1229-1239; Kamanga-Sollo et al. (2005) *Exp Cell Res* 311: 167-176; Heese et al. (2005) *Neuro-oncol.* 7: 476-484; He et al. (2005) *Am J. Physiol.* 289: H968-H972; Beattie et al. (2005) *Stem. Cells* 23 489-495; Sekiya et al. (2005) *Cell Tissue Res* 320: 269-276; Weidt (2004) *Stem Cells* 22: 890-896; Encabo et al (2004) *Stem Cells* 22: 725-740; and Buytaeri-Hoefen et al. (2004) *Stem Cells* 22: 669-674, the entire text of each of which is incorporated herein by reference.

Functional variants of the above-mentioned cytokines can also be employed in the invention. Functional cytokine variants would retain the ability to bind and activate their corresponding receptors. Variants can include amino acid substitutions, insertions, deletions, alternative splice variants, or fragments of the native protein. For example, NK1 and NK2 are natural splice variants of HGF, which are able to bind to the c-MET receptor. These types of naturally occurring splice variants as well engineered variants of the cytokine proteins that retain function are contemplated by the invention.

In some embodiments, the administration of stem cells to a subject in need thereof is accompanied by the administration of one or more cytokines to the heart. The cytokines may be selected from the group consisting of stem cell factor (SCF), granulocyte-colony stimulating factor (G-CST), granulocyte-macrophage colony stimulating factor (GM-CSF), stromal cell-derived factor-1, steel factor, vascular endothelial growth factor, macrophage colony stimulating factor, granulocyte-macrophage stimulating factor, hepatocyte growth factor (HGF), insulin-like growth factor-1 (IGF-1), Interleukin-3, or any cytokine capable of the stimulating and/or mobilizing stem cells. In a preferred embodiment, the cytokines are selected from HGF, IGF-1, functional variants of HGF or IGF-1, or combinations thereof. The cytokines may be delivered simultaneously with the $CD271^+$ population of stem cells. Alternatively, the administration of the cytokines may either precede or follow the administration of the stem cells by a specified time period. The time period may be about 15 minutes, about 30 minutes, about 1 hour, about 3 hours, about 6 hours, about 12 hours, about 24 hours, about 36 hours, about 1 week, about 2 weeks, about 1 month, or about 6 months.

The cytokines may be delivered to the heart by one or more administrations. In one embodiment, cytokines are delivered by a single administration. In another embodiment, multiple administrations of the same dosage of cytokines are delivered to the heart. A preferred embodiment of the invention includes administration of multiple doses of the cytokines to the heart, such that a chemotactic gradient is formed. A chemotactic gradient extending from the atria and/or apex of the heart to the mid-region of the left ventricle may be established by administering multiple doses of increasing cytokine concentration. Alternatively, the chemotactic gradient can be formed from the site of implantation of the stem cells to the mid-region of the left ventricle or the border region of infarcted myocardium.

In one embodiment, at least two cytokines are used in the formation of the chemotactic gradient. In another embodiment, the concentration of the first cytokine remains constant while the concentration of the second cytokine is variable, thereby forming the chemotactic gradient.

In a preferred embodiment, the chemotactic gradient is formed by multiple administrations of IGF-1 and HGF, wherein the concentration of IGF-1 remains constant and the concentration of HGF is variable. In some embodiments, the variable concentrations of HGF may range from about 0.1 to about 400 ng/ml. In other embodiments, the concentration of IGF-1 may be from about 0.1 to about 500 ng/ml.

The isolated $CD271^+$ population of stem cells and cytokines may be administered to the heart by injection. The injection is preferably intramyocardial. As one skilled in the art would be aware, this is the preferred method of delivery for stem cells and/or cytokines as the heart is a functioning muscle. Injection by this route ensures that the injected material will not be lost due to the contracting movements of the heart.

In a further aspect of the invention, the stem cells and/or cytokines are administered by injection transendocardially or trans-epicardially. This preferred embodiment allows the cytokines to penetrate the protective surrounding membrane, necessitated by the embodiment in which the cytokines are injected intramyocardially. Another preferred embodiment of the invention includes use of a catheter-based approach to deliver the transendocardial injection. The use of a catheter precludes more invasive methods of delivery wherein the opening of the chest cavity would be necessitated. As one skilled in the art would appreciate, optimum time of recovery would be allowed by the more minimally invasive procedure. A catheter approach involves the use of such techniques as the NOGA catheter or similar systems. The NOGA catheter system facilitates guided administration by providing electromechanic mapping of the area of interest, as well as a retractable needle that can be used to deliver targeted injections or to bathe a targeted area with a therapeutic. Any of the embodiments of the present invention can be administered through the use of such a system to deliver injections or provide a therapeutic. One of skill in the art will recognize alternate systems that also provide the ability to provide targeted treatment through the integration of imaging and a catheter delivery system that can be used with the present invention. Information regarding the use of NOGA and similar systems can be found in, for example, Sherman (2003) *Basic Appl. Myol.* 13: 11-14; Patel et al. (2005) *The Journal of Thoracic and Cardiovascular Surgery* 130: 1631-38; and Perrin el al. (2003) *Circulation* 107: 2294-2302; the text of each of which are incorporated herein in their entirety. In another embodiment, the isolated cardiac stem cells are administered by an intracoronary route of administration. One of skill in the art will recognize other useful methods of delivery or implantation which can be utilized with the present invention, including those described in Dawn et al, (2005) *Proc. Natl. Acad. Sci.* USA 102, 3766-3771, the contents of which are incorporated herein in their entirety.

The methods of the present invention are useful for the treatment of cardiovascular disease, including, but not limited to, atherosclerosis, ischemia, hypertension, restenosis, angina pectoris, rheumatic heart disease, congenital cardiovascular defects, age-related cardiomyopathy, and arterial inflammation and other disease of the arteries, arterioles and capillaries. Specifically, the methods of the present invention provide for the repair and/or regeneration of damaged myocardium resulting from one of the diseases listed above or from the general decline of myocardial cells with age.

The present invention also encompasses methods of preventing or treating heart failure in a subject comprising administering an isolated, $CD271^+$ population of adult cardiac stem cells into the subject's heart and administering azo angiotensin II receptor antagonist. In one embodiment, the $CD271^+$ population adult cardiac stem cells are activated prior to administration by exposure to one or more cytokines as described herein. In another embodiment, one or more cytokines are administered to the heart to form a chemotactic gradient causing the administered adult cardiac stem cells to migrate to areas of myocardial damage. In another embodiment, the one or more cytokines are HGF, IGF-1, or variants thereof. The renin-angiotensin system (RAS) is a hormone system that facilitates the regulation of blood pressure and extracellular volume in the body. When renal perfusion drops, cells in the kidney release the enzyme renin. Renin cleaves angiotensinogen, an inactive precursor peptide secreted by the liver, into angiotensin I. Angiotensin I is subsequently converted into angiotensin II (Ang II) by angiotensin-converting enzyme (ACE), which is predominantly found in the lungs. Ang II produces many effects, including vasoconstriction and secretion of aldosterone and vasopressin, through activation of the ATI receptor. Ang II has been implicated in the age-dependent accumulation of oxidative damage in the heart (Fiordaliso et al. (2001) *Diabetes* 50: 2363-2375; Kajstura et al. (2001) *Diabetes* 50: 1414-1424), and has been reported to induce senescence and decrease the number and function of endothelial progenitor cells (Kobayashi et al. (2006) *Hypertens. Res.* 29: 449-455). In addition, Ang II triggers apoptosis in myocytes (Leri et al. (1998) *J. Clin. Invest.* 101: 1326-1342) and may contribute to the progression of heart failure (McMurray et al. (2003) *Lancet* 362: 767-771). In fact, inhibition of ATI receptors has been shown to improve the clinical outcome of patients with chronic heart failure and prolong life in humans (McMurray et al. (2003) *Lancet* 362: 767-771).

The invention provides for methods of preventing heart failure and/or treating chronic heart failure in a subject by administering an Ang II receptor antagonist in combination with administration of adult cardiac stem cells to the subject's heart. Preferably, the Ang II receptor antagonist is an antagonist of the ATI receptor. Some non-limiting examples of Ang II receptor antagonists that would be encompassed by the invention include Valsartan, Telmisartan, Losartan, Irbesartan, Olmesartan, Candesartan, and Eprosartan.

In addition, inhibitors of angiotensin converting enzyme (ACE) may be administered in addition to or instead of the Ang II receptor antagonist. As described above, ACE converts angiotensin I into angiotensin II. Inhibition of this enzyme would lead to decreased levels of Ang II and thus reduce the deleterious effects of Ang II on cardiac stem cells. ACE inhibitors which may be used in the methods of the prevent invention include, but are not limited to, Benazepril, Enapril, Lisinopril, Captopril, Fosinopril, Ramipril, Perindopril, Quinapril, Moexipril, and Trandolapril.

The Ang II receptor antagonists or ACE inhibitors may be administered to the subject in multiple doses subsequent to the administration of the adult cardiac stem cells. The antagonists or inhibitors may be taken on a routine schedule for a set period of time. For example, the inhibitors may be taken once daily for about 1 month, about 2 months, about 3 months, about 6 months, about 12 months, or about 24 months after administration of the adult cardiac stem cells. Other dosing schedules may be employed. One of skill in the art, particularly a physician or cardiologist, would be able to determine the appropriate dose and schedule for the administration of the ACE inhibitors or Ang II receptor antagonists. Preferably, one or more symptoms of heart failure is reduced or alleviated following administration of the cardiac stem cells and the angiotensin II receptor antagonist and/or ACE inhibitor. Symptoms of heart failure include, but are not limited to, fatigue, weakness, rapid or irregular heartbeat, dyspnea, persistent cough or wheezing, edema in the legs and feet, and swelling of the abdomen.

The invention also comprehends methods for preparing compositions, such as pharmaceutical compositions, including adult stem cells and/or at least one cytokine, for instance, for use in inventive methods for treating cardiovascular disease, heart failure or other cardiac conditions. In one embodiment, the pharmaceutical composition comprises isolated human cardiac stem cells and a pharmaceutically acceptable carrier. In a preferred aspect, the methods and/or compositions, including pharmaceutical compositions, comprise effective amounts of adult cardiac stem cells or two or more cytokines in combination with an appropriate pharmaceutical agent useful in treating cardiac and/or vascular conditions.

In an additionally preferred aspect, the pharmaceutical compositions of the present invention are delivered via injection. These routes for administration (delivery) include, but are not limited to, subcutaneous or parenteral including intravenous, intraarterial (e.g. intracoronary), intramuscular, intraperitoneal, intramyocardial, transendocardial, trans-epicardial, intranasal administration as well as intrathecal, and infusion techniques. Accordingly, the pharmaceutical composition is preferably in a form that is suitable for injection. When administering a therapeutic of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion, and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds. Sterile injectable solutions can be prepared by incorporating the compounds utilized in practicing the present invention in the required amount of the appropriate solvent with various amounts of the other ingredients, as desired.

The pharmaceutical compositions of the present invention, e.g., comprising a therapeutic dose of $CD271^+$ stem cells, can be administered to the subject in an injectable formulation containing any compatible carrier, such as various vehicles, adjuvants, additives, and diluents; or the compounds utilized in the present invention can be administered parenterally to the subject in the form of slow-release subcutaneous implants or targeted delivery systems such as monoclonal antibodies, iontophoretic, polymer matrices, liposomes, and microspheres. The pharmaceutical compositions utilized in the present invention can be administered orally to the subject. Conventional methods such as administering the compounds in tablets, suspensions, solutions, emulsions, capsules, powders, syrups and the like are usable. Known techniques which deliver the compound orally or intravenously and retain the biological activity are preferred.

In one embodiment, a composition of the present invention can be administered initially, and thereafter maintained by further administration. For instance, a composition of the invention can be administered in one type of composition and thereafter further administered in a different or the same type of composition. For example, a composition of the invention can be administered by intravenous injection to bring blood levels to a suitable level. The subject's levels are then maintained by an oral dosage form, although other forms of administration, dependent upon the subject's condition, can be used. The quantity of the pharmaceutical composition to be administered will vary for the subject being treated. In a preferred embodiment, $2\times10^4$ to about $1\times10^5$ adult cardiac stem cells and, optionally, 50-500 μg/kg per day of a cytokine or variant of said cytokine are administered to the subject. However, the precise determination of what would be considered an effective dose may be based on factors individual to each subject, including their size, age, area of damaged myocardium, and amount of time since damage. Thus, the skilled artisan can readily determine the dosages and the amount of compound and optional additives, vehicles, and/or carrier in compositions to be administered in methods of the invention. Typically, any additives (in addition to the active stem cell(s) and/or cytokine(s)) are present in an amount of 0.001 to 50 wt % solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Of course, for any composition to be administered to an animal or human, and for any particular method of administration, it is preferred to determine therefore: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. The time for sequential administrations can be ascertained without undue experimentation. Examples of compositions comprising a therapeutic of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Pharmaceutical compositions of the invention are conveniently provided as liquid preparations, e.g., isotonic aqueous solutions, suspensions, emulsions or viscous compositions which may be buffered to a selected pH.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form). Solutions, suspensions and gels normally contain a major amount of water (preferably purified water) in addition to the active compound. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected. Those skilled in the art will recognize that the components of the compositions should be selected to be chemically inert with respect to the active compound. This will present no problem to those skilled in chemical and pharmaceutical principles, or problems can be readily avoided by reference to standard texts or by simple experiments (not involving undue experimentation), from this disclosure and the documents cited herein.

Compositions can be administered in dosages and by techniques well known to those skilled in the medical and veterinary arts taking into consideration such factors as the age, sex, weight, and condition of the particular subject, and the composition form used for administration (e.g., solid vs. liquid). Dosages for humans or other mammals can be determined without undue experimentation by the skilled artisan, from this disclosure, the documents cited herein, and the knowledge in the art. Suitable regimes for initial administration and further doses or for sequential administrations also are variable, may include an initial administration followed by subsequent administrations; but nonetheless, may be ascertained by the skilled artisan, from this disclosure, the documents cited herein, and the knowledge in the art.

The pharmaceutical compositions of the present invention are used to treat heart failure and cardiovascular diseases, including, but not limited to, atherosclerosis, ischemia, hypertension, restenosis, angina pectoris, rheumatic heart disease, congenital cardiovascular defects and arterial inflammation and other diseases of the arteries, arterioles and capillaries or related complaint. Accordingly, the invention involves the administration of adult stem cells as herein discussed, alone or in combination with one or more cytokines or variant of said cytokine, as herein discussed, for the treatment or prevention of any one or more of these conditions or other conditions involving heart disease or disorders. Advantageous routes of administration involves those best suited for treating these conditions, such as via injection, including, but are not limited to subcutaneous or parenteral including intravenous, intraarterial, intramuscular, intraperitoneal, intramyocardial, transendocardial, transepicardial, intranasal administration as well as intrathecal, and infusion techniques.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Materials and Methods

Non-Standard Abbreviations and Acronyms: Bone Marrow (BM); Colony Forming Unit Fibroblast (CFU-F); Coronary Artery Bypass Grafting (CABG); Ejection Fraction (EF); End Diastolic Volume (EDV); End Systolic Volume (ESV); Mesenchymal Stem Cell (MSC); Mononuclear Cell (MNC); Mouse Heart Stromal Cell Conditioned Media (MsHrtStr CM); Myocardial Infarction (MT); Non adherent MSC (NA-MSC); Recombinant human basic fibroblast growth factor (rhbFGF).

Mice: Human cells were transplanted into NOD/SCID mice subject to left coronary artery ligation and induction of myocardial infarction (MI). Only male, 2 month old mice were studied. The cohorts were as follows: 1) 10 mice injected with human MSC; 2) 10 mice injected with human BM-CD271$^+$ cells.

Method for Ligation of the Left Coronary Artery: The mice were anesthetized with 5% isoflurane for induction and then etomidate 20 mg/kg i.p. Endotracheal intubation was performed and the mouse was then placed on a cardiac monitor and ventilated mechanically. The skin over the site of left lateral thoracotomy was prepped and draped in sterile fashion using providone-iodine 10% solution. A heating pad was used to keep mice warm during procedures to prevent heat loss. Surgically sterile non-medicated ophthalmic ointment was applied to the eyes preoperatively to prevent corneal drying.

Once adequate sedation was achieved, the chest was opened via left lateral thoracotomy. The left coronary artery was exposed and ligated to produce an anterior MI. 10 minutes after occlusion erythropoietin (2-6 μg/kg) was infused through an internal jugular catheter. The chest was closed in layers with 0 and 3.0 (for muscle) absorbable suture, and buprenorphine (0.05-0.1 mg/kg s.c.) were given post-operatively for pain. Mice were bandaged and kept in standard sterile isolated housing where they recover for 3 to 4 days following surgery. Pain control was achieved with buprenorphine 0.05-0.1 mg/kg s.c. q12 h×6 doses. Animals were monitored closely (4 times daily) for pain and infection in the postoperative period, looking for signs such as anorexia, failure to groom, aggressiveness, and labored breathing. Animals that exhibited paralysis, open sores, labored breathing or reluctance to move were removed from the study and euthanized.

Sham-operated mice that experience all but the placement of the coronary artery ligature serve as controls. Perioperative mortality was low in the sham group (<15%), and slightly higher for the infarcted cohorts. Of the remaining mice, about 75% survived at least two months post-MI. The mice were typically studied for four weeks after surgery.

Stem cells were administered by direct intra-myocardial injection using a 30 gauge needle. On the day of infarction, while the chest was open for MI induction, the cells were injected directly into the myocardium. Three injections of 100 μl were delivered.

Method for Hemodynamic Measurements: Intact heart hemodynamic analysis was performed using miniaturized conductance micromanometry. Animals were anesthetized as follows: isoflurane gas followed by etomidate 12 mg/kg i.p., urethane 600 mg/kg i.p. and morphine 1 mg/kg i.p. Endotracheal intubation was performed and the mouse was then placed on a cardiac monitor and ventilated mechanically. The left internal jugular vein was exposed and cannulated with a 30 gauge needle for the administration of drugs. A 4-electrode pressure-volume catheter (SPR-839, Instruments Inc) was inserted into the right carotid artery and advanced into the left ventricle. Measurements of pressure volume loops were made at baseline and after infusion of isoproterenol (1 to 100 ng/min). Lastly, preload was decreased by clamping the inferior vena cava through a thoracic incision. Depth of anesthesia was monitored by observing chest wall movement, heart rate, blood pressure, muscle tone, and stimulus perception. At the end of the experiments, the animal (under deep anesthesia as above) was euthanized and the heart harvested for future molecular biology studies and immunohistochemistry.

Model of chronic ischemic cardiomnyopathy: Gottingen mini swine (25-30 kg, female, 10-12 months of age) were used and subjected to a large animal model of ischemic heart failure. To create the preclinical model of chronic ischemic cardiomyopathy, the minipig was given ketamine for induction of anesthesia, endotracheal intubation was performed, and isoflurane given for maintenance of general anesthesia. The pigs have continuous monitoring of noninvasive BP, heart rate, temperature, pulse oximetery, and capnography. A longitudinal incision in the mid-neck is made and the right common carotid artery and internal jugular vein were exposed. Proximal and distal control with vessel loops is obtained, and a 7 Fr vascular access sheath was then placed in both the right common carotid artery and right internal jugular vein. Pressure volume loops with IVC occlusion were obtained pre and post MI. Left and right coronary angiograms were conducted with a JR 4 catheter. Then the minipigs undergo experimental anterior wall infarction by balloon occlusion of the left anterior descending (LAD) coronary artery just distal to the first diagonal branch for 2.5 hours. The pig was monitored for arrhythmias and Advanced Cardiac Life Support initiated if necessary. At the completion of balloon angioplasty the carotid artery is repaired with 6-0 prolene sutures and the internal jugular vein ligated. The neck incision is closed in 3 layers; the fascia, subcutaneous tissue and skin are re-approximated with 3-0 polysorb. The mini pig was then recovered and the scar, typically a transmural infarction approximately 20% of the left ventricle and localized to the anteroseptal wall, was allowed to heal for 3 months as the heart undergoes remodeling.

Delivery of human BM-MSCs or human BM-CD271$^{+}$ cells: At 3 months post-MI, the minipig was given ketamine for induction of anesthesia, placed supine on the operating table, given isoflurane via a mask, endotracheal intubation was performed, and continued on isoflurane for maintenance of general anesthesia. Vascular access of the left common carotid artery and internal jugular vein was obtained as described above to conduct hemodynamic assessment with pressure-volume loops. A left anterior-lateral thoracotomy incision was made in the 5-6th intercostal space with a number 10 scalpel; the soft tissues were dissected with electrocautery to control bleeding; the parietal pleura was identified; using metzenbaum scissors it was opened to enter the left pleural cavity with care not to injure the lung parenchyma; a rib retractor was used to spread the ribs. The pericardium was identified and a longitude incision was made with metzenbaum scissors with care to stay anterior to the phrenic nerve and not injure the myocardium. The heart was exposed and 10 injections to the area of scar and border zone was done with a syringe filled with 0.5 cc of MSC or CD271$^{+}$ cells. Total injected volume was 5 cc. Any areas of bleeding were controlled with pledgeted sutures. The thoracotomy incision was closed in three layers with 2-0 polysorb sutures with an 18 Fr chest tube to underwater suction placed in the lateral aspect of the incision. The pig was then weaned from the ventilator and recovered. The chest tube was removed the next day. The cohorts were as follows: 1) Injection of 200 million MSCs at 3 months post MI (n=6); 2) injection of 2 million CD271$^{+}$ cells at 3 months post MI (n=6).

Assessment of cardiac function: The effects of transplanted CD271$^{+}$ cells and MSCs were evaluated with left ventricle pressure volume loops and serial cardiac MR. Left ventricle (LV) hemodynamics were assessed with a Millar pressure-volume transducer catheter placed into the IN during cardiac catheterization at pre and post acute MI, at the time of injection, and at sacrifice. Concurrent non-invasive cardiac function data was acquired with the use of a Siemens 1.5T MRI scanner. Cardiac MR has emerged as a comprehensive and highly accurate imaging modality to evaluate global function, regional function, scar size, and perfusion parameters. Many consider cardiac MR to be a one-stop-shop for imaging the heart as numerous cardiac parameters are assessed with one study. The cardiac MR protocol includes ECG-gated cine images, first-pass gadolinium perfusion imaging, tagged MR images, and delayed hyperenhancement images. The typical MR scan obtains approximately 1,200 images of the heart that requires extensive post-processing analysis. All images were maintained on the University of Miami WebPax system and each study downloaded to a Dell Precision 690 workstation. Two FDA approved software programs were used for the analysis, Segment (Medviso AB and Lund University, Lund, Sweden) and Diagnosoft (Cary, NC). The cine and delayed enhancement images were analyzed using the Segment Software. The tagged images and first pass perfusion images were analyzed with the Diagnosoft program to obtain peak eularian circumferential strain and myocardial upslope and area under the curve, respectively.

Sacrifice and histology: At 3 months after injection of cells each animal was sacrificed under deep anesthesia as discussed above. The heart was arrested by central infusion of 40 mEq of potassium chloride which arrests the heart in diastole. The pig's hearts were harvested and preserved in formaldehyde. Each heart was sectioned in the short axis and biopsies of the infarct, border zone, and remote zone were analyzed with confocal microscopy for engraftment and differentiation. In addition, whole body necropsy of the pigs was done to evaluate for ectopic tissue formation.

Mice: NOD-SCID mice were used since they are immunodeficient and an appropriate recipient of human stem cells. Cardiac function of mice that have undergone an MI was less than sham-operated mice within four weeks after surgery. Based on calculations S mice need to be included in each cohort to achieve a power of 0.90 and a 0.05. However, mortality after MI for wildtype mice was about 25% over the first six weeks post-operatively. Thus, in order to perform MI studies at least IO mice were used for each cohort.

Swine: Gottingen mini-swine were used in preclinical studies because of the similar coronary anatomy to a human, and at approximately 12-15 months of age it has a stable growth curve allowing them to be followed in long to survival studies with minimal confounding growth of the heart. Calculations showed that 6 pigs were needed to be included in each cohort to achieve a power of 0.90 and $\alpha$=0.05.

Mouse Surgeries: Mouse surgeries were performed with concern for the prevention of pain and discomfort. As indicated above, appropriate agents were used during any surgical procedures to provide anesthesia and analgesia. For coronary artery ligation, the mice were anesthetized with 5% isoflurane for induction and then etomidate 20 mg/kg i.p. Pain control was achieved with buprenorphine 0.05-0.1 mg/kg s.c. q12 h. In addition, mouse body temperature was maintained using warming blankets or lamps. Although some mice developed cardiac hypertrophy and heart failure due to the different surgical procedures, mice that experienced excessive weight loss, labored breathing, cyanosis and non-responsiveness were assessed, and if appropriate, euthanized early.

Swine Surgeries: All pig procedures were conducted with concern for the prevention of pain and suffering. As discussed above all procedures are conducted under general anesthesia. Post operative pain was controlled with a post-operative injection of buprenorphine 0.05-0.1 mg/kg subcutaneous and a fentanyl 25 mcg patch is placed on the dorsum of the pig for 72 hours. If at any time during the course of the study a pig was in distress it was assessed by the veterinarian and investigative team. Many cases of distress are due to an infection of the wound or lungs which can be managed with oral or intramuscular antibiotics.

Euthanasia: These methods are consistent with the recommendations of the 2007 American Veterinary Medical Association Guidelines on Euthanasia.

All swine and mice were euthanized for one of two indications: 1) exhibiting significant post-operative pain or distress which was not alleviated by analgesics, antibiotics and other measures; 2) completing the amount of time designated for the study of physiology. Mice were euthanized with an overdose of ketamine (150 mg/kg) and xylazine (10 mg/kg) and then by cervical dislocation. Swine were placed under deep anesthesia as discussed previously and the heart is arrested with 40 mEq of potassium chloride.

Example 1: Comparison of Human BM-MSCs and BM-CD271$^+$ Cells in a Mouse Model (NOD/SCJD) of Myocardial Infarction To test this, an established mouse model of myocardial infarction was used by open chest temporary ligation of the left anterior descending (LAD) coronary artery in NOD/SCID mice. After 1 hour of ischemia the suture ligation was removed from the LAD to allow full reperfusion. Mice were then randomized in a 1:1 fashion to human BM-MSCs or BM-271 1 cells. Additional groups of animals were used to establish appropriate controls and comparisons. These include CD34$^+$ and CD133$^+$ bone-marrow derived cells, which contain hematopoietic stem/progenitor cells and endothelial precursors. Following reperfusion, the cells were then injected under direct vision to the area of scar and border zone for a total injectate volume of 10 μL. The mice were then followed for 8 weeks by serial echocardiography to evaluate efficacy of cell therapy. At 8 weeks post injection, the mice undergo detailed hemodynamic evaluation, are sacrificed and the hearts harvested for immunohistochemical analysis to determine engraftment and differentiation of injected cells.

Histopathology: After hemodynamic measurements at the end of the study, the mouse heart was perfused with potassium chloride and fixatives for immunohistochemical studies. Total carcass, heart, lung and liver weights and tibial length were measured to detect hypertrophy of the non-infarcted ventricular tissue. Heart sections were stained with hematoxylin and eosin for general inspection. The fraction of the circumference of the left ventricle in transverse sections stained blue by Masson's provides a measure of infarct size.

Differentiated stem cells were tracked by immunostaining. Human cells were detected within the mouse hearts using alu staining. Staining for troponin I, α-sarcomeric actin, cardiac myocyte, desmin, α-cardiac actinin, connexin-43, GATA-4, Nkx-2.5, and MEF2 indicated myocytes. CD31 and vimentin staining was used to identify endothelial cells, while α-smooth muscle actin and SMA22 were used to identify smooth muscle cells. Thus, all cells resulting from injection of human CD71 or MSC and the potential for these cells to regenerate different lineages can be identified.

A thorough description of cardiac regeneration also included measuring total myocyte cell numbers and size. The number of myocytes per left, ventricle was estimated by counting nuclei using the method of Bruel and Nyengaard. In order to measure myocyte cross-sectional area, slides were stained with fluorescein-conjugated wheat germ agglutinin (Invitrogen) and Hoechst 33258. Myocyte volume was calculated using a combination of the Cavalieri and dissector principles. Alternatively, individual myocytes can be measured by confocal microscopy after acute dissociation using morphometric software. In order to detect the fibrosis associated with pathologic remodeling, sections were stained with sirius red (collagen) and fast green (cells). Results were corroborated by Masson's trichrome. In order to detect any apoptotic myocytes that might be associated with ongoing remodeling, paraffin-embedded sections were stained using the Apoptag Red In Situ Apoptosis Detection Kit (Millipore) based on the indirect TUNEL method. Other assays include immunohistochemistry with an antibody specific for cleaved caspase-3, detection by Western blotting of caspase-dependent PKCδ cleavage, and DNA laddering.

Mouse studies: Human BM-CD271 cells injected into the heart of NOD/SCID mice following experimental MI improves ejection fraction (EF) and fractional shortening were compared to placebo and mesenchymal stem cells. Importantly, CD271 cells were highly potent improving EF and ameliorating increases in heart chamber size to a greater degree than a much higher number of cultured MSCs. CD271 cell injections also caused improved myocardial contractility compared with placebo, as evidenced by the increased slope and left-ward shift of the end-systolic pressure volume curve. When evaluated histologically, CD271 cells exhibited a high degree of engraftment and evidence of myocyte differentiation, supporting the idea that cardiac recovery is due to cell engraftment in the injured myocardium. These studies definitively test the hypothesis that CD271 MSC precursors are capable of myocyte and vascular differentiation, and repair of the injured heart to a greater degree than cultured MSCs.

Example 2: Comparison of Human BM-MSCs and BM-CD271$^+$ Cells in a Pig Model of Myocardial Infarction A large animal model of chronic ischemic cardiomyopathy was used and is well-established in this laboratory (7, 8) to test whether CD271 cells engraft and differentiate into myocytes, endothelial cells, and vascular smooth muscle cells. Cardiac MRI was also used to test the effects of CD271$^+$ cells on cardiac function, scar size and myocardial perfusion. The inventors have extensive experience in creating models of ischemic cardiomyopathy in various breeds of swine (8, 9). For this study, 10 adult Gottingen mini-swine undergo experimental balloon angioplasty of the left anterior descending coronary artery for 2.5 hours, resulting in a transmural infarct of the anterior-septa wall encompassing approximately 20% of the left ventricular myocardium, followed by full reperfusion upon balloon deflation. The animals were then recovered and followed with serial cardiac MR as the heart undergoes extensive remodeling. At 3 months post M1, the pigs were randomized in a 1:1 fashion to human BM-MSCs or human BM-CD271$^{+}$ cells. Animals then have a left mini-thoracotomy where human bone marrow derived CD271$^{+}$ cells or MSCs were injected under direct vision with a 22 gauge needle. Any areas of bleeding were suture ligated. The chest was then closed and the animals serially followed with cardiac MR. All mini-swine were immunosupressed with oral cyclosporine A (CsA) to prevent immune rejection from xenotransplantion of human cells into a pig heart (10, 11).

The efficacy of CD271$^{+}$ cells was assessed with serial cardiac magnetic resonance imaging (MRI). This imaging modality allowed detailed phenotypic analysis of global cardiac function, regional cardiac function employing HARP, scar size using delayed hyper-enhancement imaging, and myocardial perfusion upslope and area under the curve by first pass perfusion of gadolinium. At 3 months following injection, the animals were sacrificed and the hearts harvested for immunohistochemical analysis to determine engraftment and differentiation of CD271$^{+}$ cells. Whole body necropsy was performed on each animal to evaluate for ectopic tissue formation.

Detailed safety and efficacy evaluation was performed in these animal studies as described (7-9). The overall goal was to establish long-term safety that includes freedom from neoplasia or ectopic tissue formation, and to add to the growing database that acute surgical delivery of cells into the failing heart was safe. Moreover, in parallel detailed mechanistic studies was performed employing imaging, hemodynamic assessment, and immunohistochemistry to test the hypotheses that CD271$^{+}$ cell injection was highly effective at creating reverse remodeling in chronic ischemic cardiomyopathy, and that the mechanism of this effect was at least in part due to cell engraftment and differentiation.

Autologous Mesenchymal Stem Cells Produce Reverse Remodeling in Chronic Ischemic Cardiomyopathy: The work in this laboratory in large animal models with fully healed scars after myocardial infarction showed that MSC administration can significantly improve left ventricular structure and functional indices, indicating meaningful repair. Through exploitation of this experience with imaging techniques phenotypic improvements triggered by implantation of MSCs were tracked in the porcine model of chronic ischemic cardiomyopathy, and quantified these changes morphometrically. MI was created in swine after 12 weeks, the infarct segment had thinned, leaving transmural scar. Autologous MSCs were expanded from each animal, and these cells or placebo were delivered to the infarct and surrounding border zone at this time. During a further 12-week follow up period, cardiac MRI revealed that intramyocardial injections of MSCs not only reduced the scar burden (mass of LV) by 21.8+3.9% ($p<0.05$ vs. placebo and week 12 vs. week 24), but also significantly improved regional contractility, global LV function, ejection fraction, and myocardial blood flow. Importantly, the therapy produced reverse remodeling and reduced the circumferential extent of the infarct scar. This constellation of effects evidences highly effective repair in ischemic cardiomyopathy.

Allogeneic Mesenchyrnal Stem Cells Restore Cardiac Function in Chronic Ischemic Cardiomyopathy Via Trilineage Differentiating Capacity: The hypothesis was tested whether MSC based cardiac repair regenerates the heart via mechanisms comprising long-term engraftment and by differentiation into both myocardial and vascular elements. Allogeneic MSCs were generated from a male swine donor, and administered sex mismatched cells by transendocardial injection into female swine 12 weeks post-MI. Animals were followed with serial MRI, and 12 weeks later the hearts were collected for immunohistological evaluation. The fate of the male donor cells was determined by co-localization of Y-chromosome ($Y^{pos}$) cells with markers of cardiac, vascular and endothelial lineages. MSCs engrafted in infarct and border zones and differentiated into cardiomyocytes as ascertained by co-localization with GATA-4, Nkx.2.5 and α-sarcomeric actin markers. In addition, $Y^{pos}$ MSCs exhibited vascular smooth muscle and endothelial cell differentiation, contributing to large and small vessel formation. The number of cells engrafting correlated with the functional changes that occurred. Long-term MSC survival, engraftment, and differentiation into myocardial, vascular, and endothelial lineages were demonstrated following transplantation into chronically scarred myocardium. The capacity of these cells' for cardiomyogenesis and vasculogenesis both likely contributed to their ability to repair chronically scarred myocardium.

Example 3: Testing of CD271$^{+}$ Cells in a Clinical Trial of Patients With a MI Undergoing Bypass Surgery and a Clinical Trial CD271$^{+}$ Cells in Patients Undergoing Bypass Surgery To be undertaken is a phase I/II clinical trial [called "Prospective Randomized Study of CD271$^{+}$ Cell Therapy in Patients Undergoing Cardiac Surgery" (PROMETHEUS-II)]. It is a double-blind, randomized, placebo-controlled trial, comparing CD271$^{+}$ cells to placebo in 15 patients undergoing bypass surgery. The endpoints of this trial are safety and efficacy. The efficacy endpoint utilizes cardiac magnetic resonance imaging (MRI) to assess myocardial infarct size, regional and global left ventricular (LV) function, and myocardial perfusion. A biorepository of patient bone marrow and circulating blood samples is also collected to determine biomarkers which may predict successful response to therapy. The CD271$^{+}$ cell products used in this trial are isolated in the Cell Manufacturing Program facilities at the University of Miami. The CD271$^{+}$ cell to use in this trial is a bone marrow derived adult stem cell that is a precursor to the MSC.

Preliminary Clinical Trial Data: Transendocardial Autologous Cells in Ischemic Heart Failure Trial (TAC-HFT): TAC-HFT is a phase I/II randomized, double blinded study that was approved by the Food and Drug Administration for enrollment in 2009. This study will enroll 60 patients with chronic ischemic left ventricular dysfunction (EF between 20-50%) secondary to a myocardial infarction. The Helix Infusion Catheter (BioCardia, San Jose, CA) is used to deliver via transendocardial injections of either: MSCs, whole bone-marrow, or placebo during cardiac catheterization.

The TAC-HFT trial was designed to enroll 8 patients as an open-label run in phase to establish preliminary safety data prior to the double-blinded randomized phase of 60 patients. These first 8 patients received either whole bone marrow (n=4) or bone marrow derived mesenchymal stem cells (n=4) in an unblinded fashion. All eight patients tolerated the stem cell injections without any major adverse events, allowing the double blinded phase to subsequently enroll patients. Since the first eight patients all received cell injections, their cardiac MR images were analyzed. Cine images and delayed enhancement images were analyzed using the software Segment (Medviso AB and Lund University, Lund, Sweden) and tagged cardiac images were analyzed using HARP software (Diagnosoft, Inc.). Preliminary data from these patients reveal that at 6 months after stem cell injection, improvements in global function demonstrated a decrease in end-diastolic volume of 11.2+3.4% ($p<0.05$), a decrease of 13.5+4.2% ($p<0.01$) in end-systolic volume, and an average increase in ejection fraction of 4.9+6.7%. On delayed enhancement images, the scar size as a percent of left ventricular mass decreased an average of 13.3+7.2% ($p=0.06$). The tagged MR images showed regional improvement in contractility in the area of infarct and border zone as demonstrated by Eulerian Circumferential Strain. These data show MSCs are safe, improve cardiac function, support reverse remodeling, and reduce scar size.

These data are precedent setting as no other therapeutic strategy achieves this degree of reverse remodeling accompanied by actual reduction of myocardial scar. These exciting, findings are highly supportive of the imperative to accelerate clinical research in this field.

A Randomized, Double-Blind, Placebo-Controlled, Dose-Escalation Study of Intravenous Adult Human Mesenchyrnal Stem Cells (Prochyrnal) After Acute Myocardial Infarction: The safety and efficacy data of the phase I study of 53 patients enrolled was recently published in the Journal of the American College of Cardiology (18) and provided pivotal safety data of allogeneic MSCs. In this trial, patients with reperfused acute MI were randomized to a single intravenous infusion of placebo or human MSCs isolated from bone marrow aspirates obtained from a single unrelated donor who was not human-leukocyte-antigen-matched to recipients. The adverse event rates were similar in hMSC treated (5.3 per patient) and placebo treated (7.0 per patient). The ambulatory ECG recordings demonstrated a reduced number of ventricular tachycardia episodes m hMSC treated patients compared to placebo. Echocardiography in anterior MI patients showed improved ejection fraction in hMSC treated patients. Importantly, this trial provided pivotal safety data for the use of allogeneic MSCs in ischemic heart disease.

Additional preclinical safety and efficacy data from the inventor's laboratory (7, 8, 15) have been obtained in a variety of breeds of porcine models with acute and chronic MI. MSC injection via catheter into infarcted tissue reduces myocardial infarct size, improves global and regional LV function, normalizes cardiac energetics, and restores tissue perfusion (7, 8, 16).

Isolation of $CD271^+$ Cells from Normal Human BM: Bone marrow aspirates were obtained from a patient's iliac crest under conscious sedation and local analgesia by an experienced Hematologist/Oncologist. The BM mononuclear cells were isolated using density gradient centrifugation and then the cells were labeled with microbeads attached to an antibody to CD271 and the $CD271^+$ cells isolated on the CliniMACS clinical device (Miltenyi Biotech, Cologne, Germany). The cells were then washed and prepared for infusion. This process takes approximately 4 to 5 hours. All $CD271^+$ cells (1-5 M) were used for patient injection.

Previous work from this laboratory has demonstrated the feasibility of isolating $CD271^+$ cells. $CD271^+$ cells were isolated from normal donor bone marrow cells using an indirect labeling of cells with anti CD271-APC and anti-APC Microbeads. The median cell number of the starting BM MNC was $1.4\times10^8$ nucleated cells (range $2.9\times10^7$ to $3.3\times10^8$, N=7) resulting in a median of $4.2\times10^5$ $CD271^+$ cells after selection (range $3.9\times10^4$ to $9.4\times10^5$). This represents a frequency of 0.3% of $CD271^+$ cells in the BM MC product. The isolated $CD271^+$ cells demonstrated a primitive morphology with a low cytoplasm to nuclear ratio. When placed into liquid culture, the $CD271^+$ cells formed MSC within 7 days, while whole BM MNCs formed fewer MSC. The generation of MSCs from $CD271^+$ cells was compared to $CD271^+$ cells and while 170,000 $CD271^+$ cells generated significant MSCs after 7 days of culture in a T162 $cm^2$ flask, one hundred times more $CD271^-$ cells ($1.7\times10^7$ cells in a T162 $cm^2$ flask) failed to generate significant MSCs in 7 day. There were some adherent cells in the culture of $CD271^-$ cells, however, these appeared to be endothelial cells not MSCs. The $CD271^+$ cells were enriched for CFU-F, with 1 in 222 $CD271^+$ cells forming CFU-F compare to 1 in 12,500 BM MNC. Also the CD271 negative fraction contained very few CFU-F with less than 1 in 100,000 cells.

Cell Delivery: At the completion of coronary artery bypass surgery, the autologous BM-$CD271^+$ cells or placebo were injected by the cardiac surgeon under direct vision via the epicardium to the area of scar and border zone. Any areas of bleeding were controlled with pledgeted sutures.

Cardiac MRI: This group has extensive experience in determining cardiac structure and function by exploiting cutting-edge, non-invasive imaging techniques (17, 19, 20). Cardiac MR was used to evaluate efficacy of cell therapy. Myocardial function, tissue perfusion and non-invasive determination of infarct size, were determined by Harmonic Phase (HARP) Tissue Tagging, gadolinium uptake kinetics, and Delayed Contrast-Enhancement MRI protocols, respectively. Patients lay supine on the magnet table and all images were obtained during a 12-15 heartbeat breathhold at end-expiration, averaging 10-15 sec with adequate rest periods between breath holds (10-15 sec). The imaging protocol first included sagital, axial and oblique scout images to localize the heart. Each MRI session is estimated to last 45-60 min. To determine myocardial function, tissue tagging protocols were performed as previously described. The protocol was based upon an ECG triggered fast gradient echo pulse sequence that resulted in 6 mm-tagged separation of the myocardium. This method, yielded quantitative motion and strain parameters on a regional basis that can be used for comparison across subjects at different time points after intervention, thus providing a rapid and repeatable method to assess serial and quantitative LV function. Next, patients received a bolus intravenous injection of 0.2 mmol/kg of gadolinium-DTPA. High-resolution delayed-enhancement images were obtained from eight to ten short-axis cross sections of the LV (ensuring entire cardiac coverage) using an inversion-recovery prepared gated fast gradient echo sequence. The acquired hyper-enhanced regions obtained with this method, have been shown to be within 10% of the infarct size measured post-mortem by triphenyl-tetrazolium chloride (TTC) staining, thus signifying this method as a very accurate way to determine infarct size (19).

Example 4: Cardiac Potential a/Bone Marrow $CD271^+$ MSC Precursor Cells

Methods

Isolation of $CD271^+$ cells: Bone marrow aspirates (25 to 50 ml) were obtained from AllCells LLC (Emeryville, CA) under appropriate informed consent and IRB approval. The bone marrow (BM) cells were diluted 1:1 with PBS+1% KS and layered over ficol to isolate the low density mononuclear cell fraction (MNC). The MNC were then labeled with CD271 microbeads (Miltenyi Biotech, Cologne, Germany) and the $CD271^+$ cells isolated using a Miltenyi MACS cell selection device (VarioMACS) according to the manufacturers recommended procedures. The $CD271^+$ cells were counted and cytospins prepared for morphological analysis.

Isolation and Expansion of Mesenchymal Stem Cells (MSCs): BM MNCs were isolated as described above and the cells were cultured in T162 $cm^2$ culture flasks at 1 to 3 million MNCs per ml of alpha MEM containing 20% FBS plus 1% glutamine penicillin and streptomycin. Media was changed every 3 to 4 days with discard of the non adherent cells. MSCs grew as adherent cells on the surface of the flasks and the cultures were passaged when confluent using trypsin treatment. The MSCs were harvested at passage 4 or 5 and frozen in liquid nitrogen. Prior to injection the cells were thawed and washed.

CFU-F Assay: The clonegenic potential of BM MNCs, $CD271^+$ and $CD271^-$ cells were assessed using the colony forming unit-fibroblast (CFU-F) assay. Cells were plated in 35 mm dishes in 2 ml of Mesenchymal Stem Cell Stimulatory Media plus supplements (Stem Cell technologies, Vancouver, Canada). Cells were plated at different cell densities ranging from 10,000 cells per plate up to 1 million cells per plate. Cultures were incubated at 37° C. in 5% $CO_2$ for 10 days and then stained with Giemsa stain and scored using a dissecting microscope. Typically CFU-F colonies are between 1 and 8 mm in diameter and can be scored macroscopically.

Induction and Assessment of Adipocytic and Osteogenic Differentiation Potential: $CD271^+$ cells were cultured under non adherent conditions in Teflon bags and the cells harvested and plated in 6-well cell culture dishes (Nunc, Roskilde, Denmark) for differentiation assays. Adipocytic differentiation was induced by culturing these cells in NH AdipoDiff Medium (Miltenyi Biotec Tnc., Auburn, CA, USA) at a concentration of $5\times10^4$ cells/ml for 2 weeks. Then cells were used for lipid droplet staining using Oil Red O (Sigma-Aldrich, St. Louis, MO). Osteogenic differentiation was induced by culturing these cells in NH OsteoDiff Medium (Miltenyi Biotec Inc.) at a concentration of $3\times10^4$ cells/ml for 3 weeks. Then the cells were stained with SIGMA FAST BCIP/NBT Buffered Substrate Tablet (Sigma) to detect their expression of alkaline phosphatase (AP), an enzyme that is involved in the bone matrix mineralization. Cells that were cultured in alpha-MEM during this period were used as controls.

Animal Model, Myocardial Infarction and cell transplantation. All experiments on live animals were performed in accordance to the protocol approved by the animal care and use program at the University of Miami. Animals were anesthetized using Isoflurane inhalation through endotracheal intubation (1-2%) while anesthesia level was controlled with body temperature and heart rate. Buprenorphine (0.3 mg/kg, SQ injection) was used at pre- and post-surgical time (Q6 hours) for pain management. Using a left anterior thoracotomy, the heart of NOD/SCID female mice (NOD/SCID; Jackson Laboratory, Bar Harbor, ME) at 8-10 weeks of age was exposed and LAD artery was ligated permanently with 7-0 prolene suture. Infarction was confirmed by visual blanking distal to ligation and ST segment elevation on electrocardiogram (ECG). The first follow up ECG was used at 48 hours after surgery as a enrollment criteria for the study so all animals had equal size MI. Four experimental groups were established consisting of animals received phosphate buffered saline (PBS) injections as control; $CD271^+$ cells ($1.2\times10^5$ cells), human BM MSCs in two different doses of $1.2\times10^5$ (low dose) or $1\times10^6$ cells (high dose). Immediately following infarction, each animal received three injections (10 μl/injection) of PBS or cells in the boundaries and the center of the infarcted region using a 30 gauge needle. Surgical mortality was 11.5% and mortality in first 48 hours after cell injection was 5% (total mortality for peri surgical time is 16.5%). Eight weeks post-transplantation the animals were sacrificed and the hearts prepared for immunohistological analysis.

Echocardiography: Cardiac function was monitored by Vevo 770 imaging system (Visual Sonic Inc., Toronto, Canada) at baseline before surgery, 48 hours, 1, 2, 4 and 8 weeks 8 after infarction and cell injection. Images were recorded under anesthesia with Isoflurane inhalation (1-2%) at heart rates above 400 bpm and body temperatures of (37±10 C). Sonographic parameters of heart structure and anatomy including end diastolic volume (EDV), end systolic volume (ESV) and ejection fraction (EF) were calculated using two dimensional images.

Pressure volume loop analysis: Eight weeks after cell injection and using the right carotid approach a Millar conductance manometry catheter (SPR 839) (Millar Instruments, TX) progressed to the left ventricle. During the procedure, a diluted 6.25% albumin solution was infused into jugular vein at a rate of 5 μl/min and anesthesia was achieved with 1-2% Isoflurane inhalation through endotracheal intubation. Pressure volume: data were obtained using MPVS Ultra system (Millar Instruments, TX) at baseline and after inferior vena cava (IVC) occlusion. The volume calibration was done using cuvette method and hypertonic saline infusion.

Tissue preparation and histopathology: After finishing PV loop recordings, hearts were harvested and perfused for 10 minutes with potassium chloride 20 μM solution and formalin 10% at 1 ml/min through aortic cannulation to fix the hearts in diastole. The hearts were sliced and histology cuts were stained with Mason Trichrome (TM) and H&E or used for immunohistochemistry.

Human specific DNA probes were used (Human Alu Probe, BioGenex, CA) and Fluorescence in Situ Hybridization (FISH) method to trace injected human cells iii the mouse tissue (AntiFluorescein-HRP Conjugate, Perkin Elmer, Boston, MA). Samples from human fetal heart and PBS injected mice were used as positive and negative controls respectively. The Alu stained slides were scanned with a Zeiss fluorescent laser scanner and the images were analyzed using Mirax viewer software at 20× magnification. Images were taken separately and merged using CS3 Adobe Photoshop and positive cells counted in two separate areas of the same cut.

Immunohistochemistry: The samples were stained with cardiac specific antibodies, alpha sarcomeric actin (a-SA) (Sigma, St. Louis, MO), Troponin I (Tnl) (Abeam, Cambridge, MA), and Connexin 43 (Cx43) (Santa Cruz, CA). Laminin (Abeam) staining was used to delineate cells. The stained samples were studied first by immunofluorescent microscopy and then confocal microscope Zeiss LSM710 to prepare images.

Statistical analysis: Data were analyzed using Graph Pad Prism software and values are expressed as average±standard error of mean (SEM). Analysis of variance was used with repeated measurements (two-way ANOVA with Bonferoni post hoc test to analyze echo data and one way ANOVA to compare terminal hemodynamic data with Newman-Keuls Multiple Comparison post hoc test.

Results

Isolation of CD271+ cells from Normal Human BM: $CD271^+$ cells were isolated from normal donor BM cells using an indirect labeling of cells with anti CD271-APC and anti-APC Microbeads. The median cell number of the starting BM MNC was $1.4\times10^8$ nucleated cells (range $2.9\times10^7$ to $3.3\times10^8$, N=7) resulting in a median of $4.2\times10^5$ $CD271^+$ cells after selection (range $3.9\times10^4$ to $9.4\times10^5$). This represents a frequency of 0.3% of $CD271^+$ cells in the BM MNC product. The isolated $CD271^+$ cells demonstrated a primitive morphology with a low cytoplasm to nuclear ratio (FIG. 1).

Figure 2A:
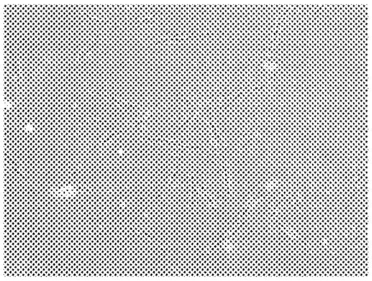
FIG. 2A shows MSC formation from CD271$^+$ cells (170,000 cells per T75 cm$^2$ flask).
Figure 2B:
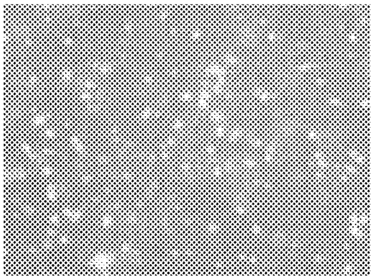
FIG. 2B shows MSC formation from BM MNCs (15 million cells per T75 cm$^2$ flask).
Figure 2C:
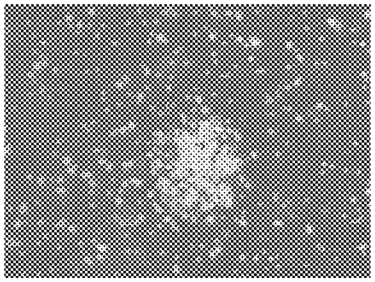
FIG. 2C shows MSC formation from CD271$^+$ cells (17 million cells per T75 cm$^2$ flask).

When placed into liquid culture, the $CD271^+$ cells formed MSC within 7 days (FIG. 2A), while whole BM MNCs formed fewer MSC (FIG. 2B). The generation of MSCs from $CD271^+$ cells were compared to $CD271^-$ cells and while 170,000 $CD271^+$ cells generated significant MSCs after 7 days of culture in a T162 $cm^2$ flask, one hundred times more $CD271^-$ cells ($1.7\times10^7$ cells in a T162 $cm^2$ flask) failed to generate significant MSCs in 7 days (FIG. 2C). As shown in FIG. 2C there were some adherent cells in the culture of $CD271^+$ cells, however, these appeared to be endothelial cells not MSCs.

Figure 3:
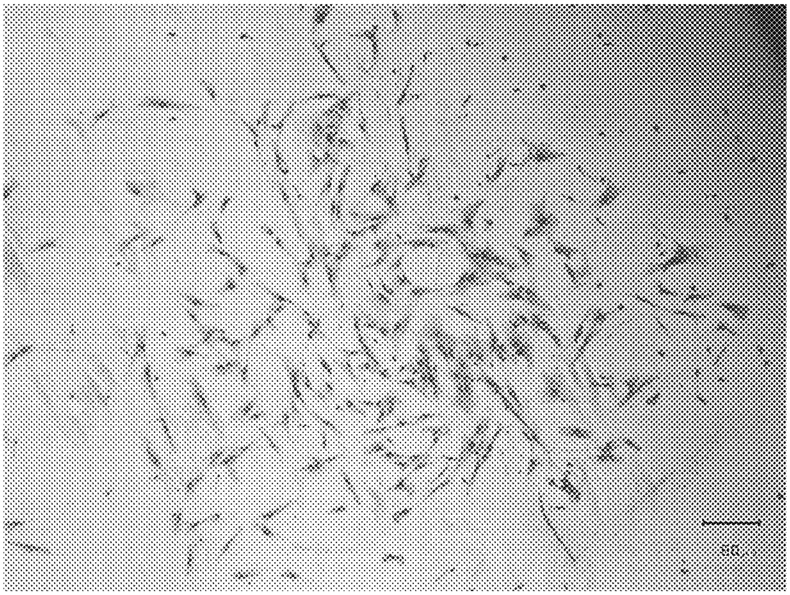
FIG. 3 shows a typical CFU-F colony at day 10 of culture.

The $CD271^+$ cells were enriched for CFU-F (FIG. 3), with 1 in 250 $CD271^+$ cells forming CFU-F compare to 1 in 12,500 BM Also the CD271 negative fraction contained very few CFU-F with less than 1 in 100,000 cells.

Figure 4:
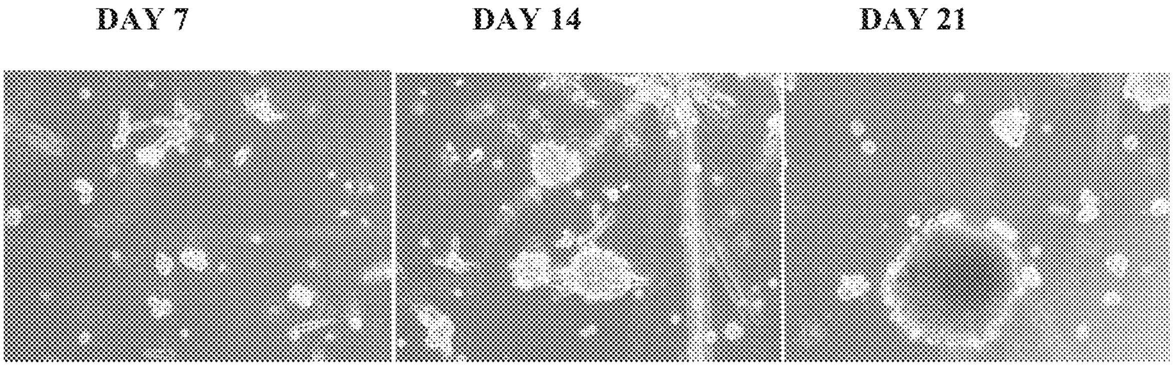
FIG. 4 shows the culture of CD271$^+$ cells in Teflon bags for 7, 14 and 21 days.
Figure 5:
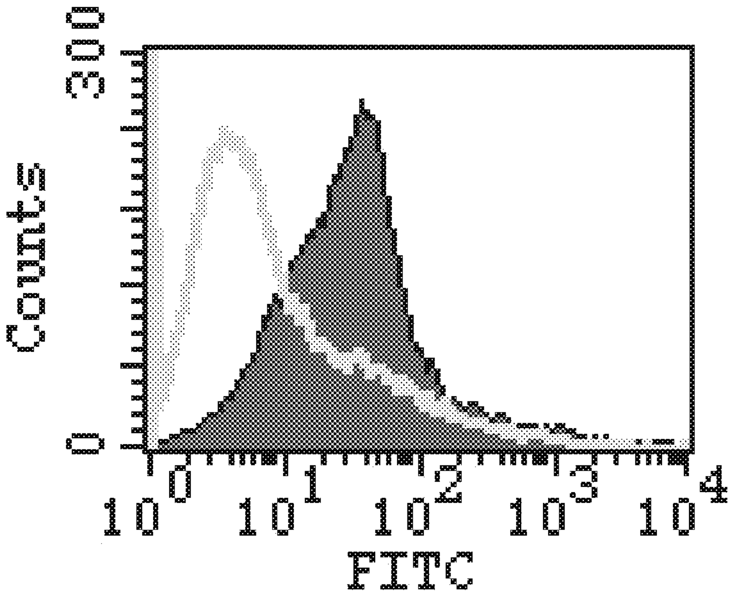
FIG. 5 shows the flow analysis of non-adherent mesenchymal stem cells (NA-MSC). Isotype control staining is shown in the green line and CD105-FITC in the shaded area.

In Vitro Culture of $CD271^+$ Cells in Non Adherent Conditions: The $CD271^+$ cells were grown in non adherent culture conditions in Teflon bags for 1 to 3 months and the early stages of growth are presented in FIG. 4. The media for these cultures consisted of alpha-MEM+20% FCS with 20 ng/ml recombinant human basic fibroblast growth factor (rhbFGF). In the first week clusters of cells could be seen with some cells forming on the surface of the Teflon bag similar in morphology to plastic adherent MSC. The bags were massaged to detach adherent cells and the media changed weekly. The clusters of cells continued to proliferate and form spheres as shown in FIG. 4 with large spheres developing by day 21. These cells were analyzed after 4 weeks in culture by flow cytometry and FIG. 5 shows that the majority expressed CD105, a typical MSC marker.

Figure 6A:
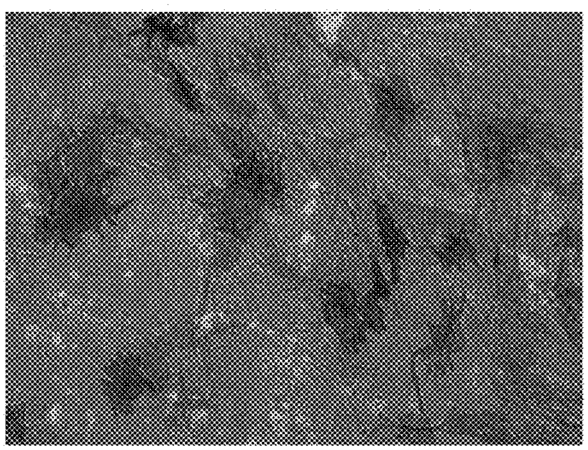
FIG. 6A shows the osteogenic differentiation from human bone marrow CD271$^+$ cells. Osteogenic differentiation was performed as described in the methods. Presence of osteogenic differentiation was shown by expression of alkaline phosphatase (AP) stained by FAST BCIP/NBT (x/100) on day 14. A representative example of three experiments is shown.
Figure 6B:
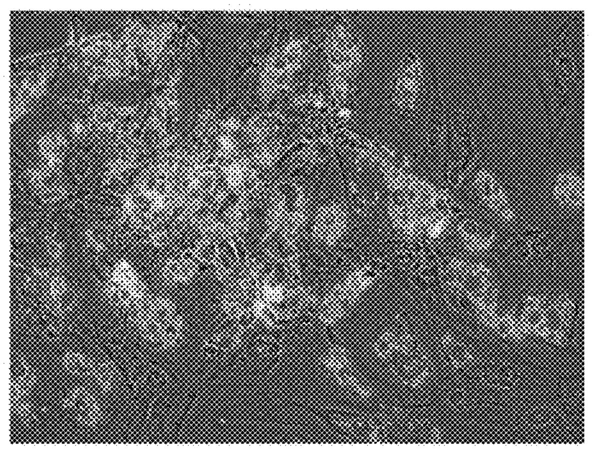
FIG. 6B shows the adipocyte differentiation from human bone marrow CD271+ cells. Adipocyte differentiation was performed as described in the methods. Differentiation to adipocyte was shown by Oil Red O staining (x/100) on day 11. A representative example of three experiments is shown.

Adipocytic and osteoblastic differentiation potential of the $CD271^+$ cells grown under non adherent conditions was also evaluated. Cells were harvested from the culture bags and plated in 6-well cell culture dishes (Nunc, Roskilde, Denmark) for differentiation assays. As shown in FIG. 6, the cultured CD271+ cells differentiated into both adipocytes and osteoblasts.

Cells were also cultured under typical MSC culture conditions, namely culture in tissue culture flasks with alpha MEM media plus 20% FCS. The spheres shown in FIG. 4 attached to the plastic surface of the flasks and typical MSCs grew from the spheres and formed confluent cultures after 1 to 2 weeks.

These results demonstrate that $CD271^+$ cells cultured under non adherent conditions form spheres of cells which are $CD105^+$, have adipocyte and osteoblast potential and form plastic adherent MSC like cells consistent with MSC properties.

Figure 7:
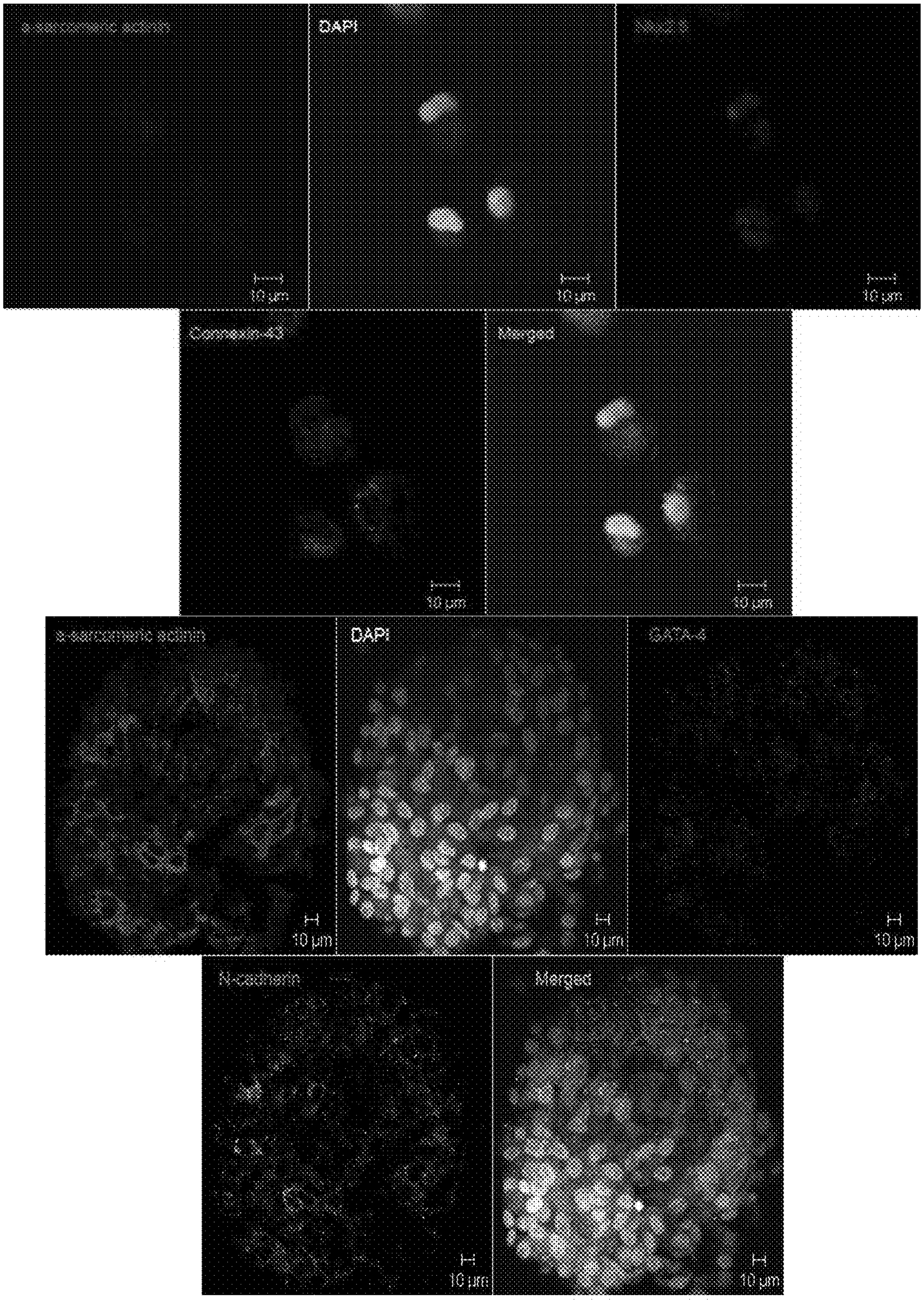
FIG. 7 shows the expression of cardiac markers in cultured CD271$^+$ cells.

Using media conditioned by mouse stromal cells derived from heart tissue (MsHtStr CM) the cardiac potential of $CD271^+$ cells cultured under non adherent conditions for 2 weeks was evaluated. The non adherent MSC (NA-MSC) expressed alpha sarcomeric actinin, Nkx2.5 and Connexin-43, GAT-4 and N-Cadherin (FIG. 7). These results demonstrate that the $CD271^+$ cells have the potential to differentiate into cardiac cells as well as adipocytes and osteoblasts and evidence that the $CD271^+$ cells have greater differentiation potential compared to MSCs generated as plastic adherent cells. As CD271 is a neural receptor it was proposed that these cells may also possess neural differentiation potential and currently undertaking experiments to evaluate this question.

Figure 8:
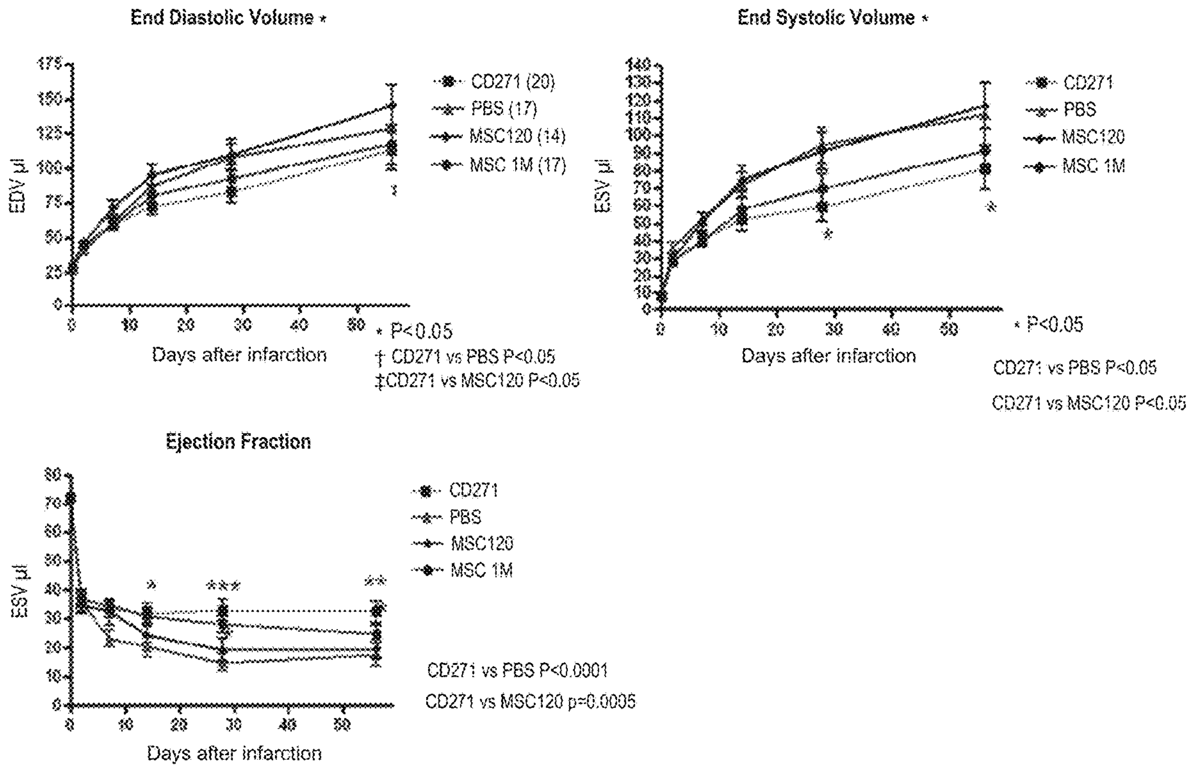
FIG. 8 shows the echocardiographic comparison of treatment groups.

In Vivo Potential of BM-$CD271^+$ Cells: To evaluate the in vivo cardiac potential of BM $CD271^+$ cells, freshly isolated human $CD271^+$ cells were injected into infracted hearts of NOD/SCID mice. The MI injury produced a time dependent ventricular dilatation and dysfunction (FIG. 8). The initial impact of infarction among all groups was equal. Comparison of ventricular volume at end diastole (EDV) (FIG. 8) showed marked reverse remodeling in the mice treated with $CD271^+$ cells (112.8+13.6 μl) when compared with control (128.1±15.7 μl)(P=0.02). The CD 271 treated group also did markedly better than animals treated with an equal dose of MSC (low dose 145.5+14.9 μl) (p=0.0001) but similar to animals treated with the high dose of MSC (116.5±14.5 μl). A dose response was demonstrated in the MSC treated animals with a significant difference between animals treated with the low dose of MSCs compared to the high dose (p=0.0001). The same trends resulted in End Systolic Volume (ESV) CD 271 treated animals had a significantly lower ESV (81.5±12.4 μl) compared to control animals (119.7±17.8 μl, p<0,0001) and low dose MSC treated animals (117.1±13.4 μl, p<0.0001) but not the high dose MSC treated animals (91.2±12.6 μl). The CD 271 treated animals demonstrated a higher ejection fraction (EF) at the end of 8 weeks (32.3±3.7%) compared to control treated animals (17.6±4.1%, p<0.0001) and low dose MSC treated animals (19.7+3.1%, p=0.0005) but not high dose MSC treated animals (24.7+2.9%).

Pressure volume loop analysis: Hemodynamic evaluation of treated and control hearts were performed at 8 weeks following injection. Conductance manometry was used through transcarotid approach. Arterial elastance (Ea) was calculated and CD271 treated mice had a lower Ea (3.0±0.2 mmHg/μL) compared to control animals (4.7+0.2 mmHg/μL, p<0.05), but not significantly different to either the low or high doses MSC treated mice (4.3±0.6 and 3.5±0.4 mmHg/μL respectively). Constant of isovolumic relaxation (Tau_Weiss) showed improved diastolic properties of CD271 hearts (12.3+0.8 msec) than controls (15.2-1.0 msec, p<0.05).

Figure 9A:
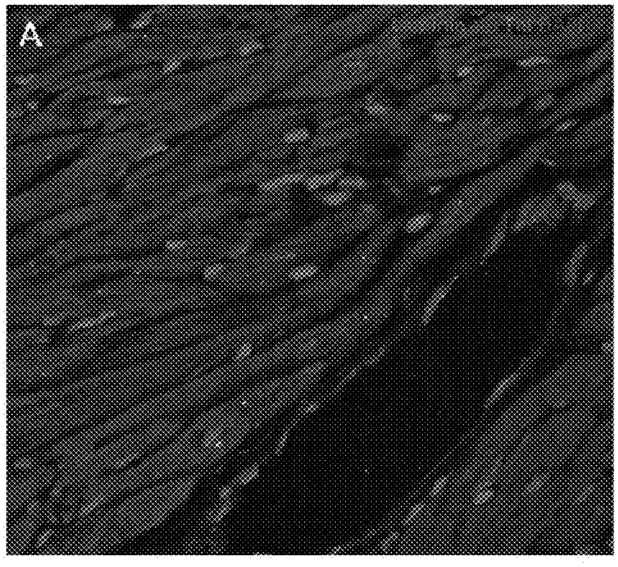
FIG. 9A shows the immunohistochemistry of a heart section from NOD/SCID mice injected with CD271$^+$ cells. The heart section was stained with Alu sequence and co stained with cardiac markers (αSA, troponin I (TnI), Connexin 43 (Cx)) (40×).
Figure 9B:
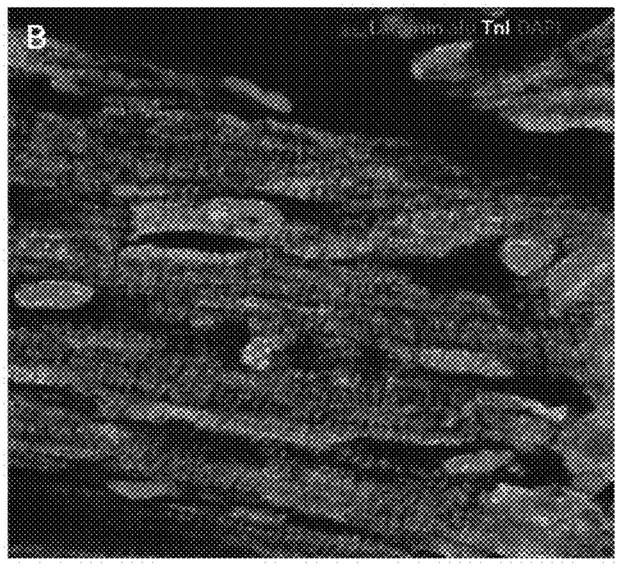
FIG. 9B shows the immunohistochemistry of a heart section from NOD/SCID mice injected with CD271+ cells. The heart section eras stained with Alu sequence and co stained with cardiac markers (αSA, troponin I (TnI), Connexin 43 (Cx)) (40×).
Figure 9C:
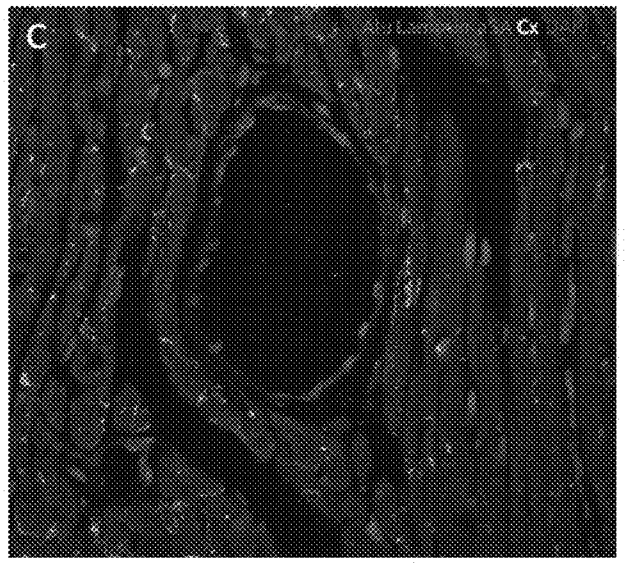
FIG. 9C shows the immunohistochemistry of a heart section from NOD/SCID mice injected with CD271+ cells. The heart section was stained with Alu sequence and co stained with cardiac markers (αSA, troponin I (TnI), Connexin 43 (Cx)) (40×).
Figure 9D:
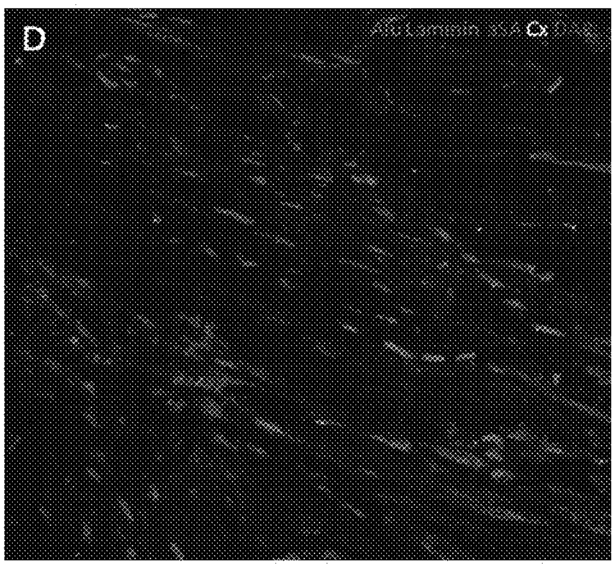
FIG. 9D shows the immunohistochemistry of a heart sections from NOD/SCID mice injected with CD271+ cells. The heart sections was stained with Alu sequence and co stained with cardiac markers (αSA, troponin I (TnI), Connexin 43 (Cx)) (40×).

Immunohistochemistry: Tissue sections from hearts of animals treated with $CD271^+$ cells, MSCs and placebo were stained with human specific Alu probes 8 weeks after injection. As shown in FIGS. 9A-9D, animals injected with $CD271^+$ cells demonstrated the presence of human cells in both remote and border zones of the hearts. A large number of human cells were detected either embedded in the vascular wall or between host cells. In addition, some cardiomyocytes were positive for Alu and Alu positive cells expressed troponin I (FIG. 9B) and alpha smooth actinin (FIG. 9D). This evidences some cardiac differentiation potential of $CD271^+$ cells. Human cells were also detected in the hearts of animals injected with the high dose of MSCs and again these cells were either embedded in the vascular wall or between host cardiomyocytes. There was no detection of Alu staining cardiomyocytes or expression of cardiac markers in Alu positive cells in the hearts of animals injected with the high dose of MSCs.

Discussion $CD271^+$ cells were present at a low frequency in BM cells consisting of approximately 0.3% of the BM MNC population. Using Miltenyi MACS selection reagents and devices, a highly purified population of CD271$^+$ cells were isolated having greater than 90% purity with an average recovery of $4.2\times10^5$ cells from a 25 cc BM aspirate. The morphology of the CD271$^+$ cells demonstrated a primitive phenotype of uniform blast cells consisting of a low cytoplasm to nuclear ratio. The data confirmed the enrichment of MSC forming cells in the CD271$^+$ population with a 60 fold higher level of CFU-F in CD271$^+$ cells compared to BM MNCs. In addition, the frequency of CFU-F in CD271 negative population was greatly reduced at 1 in 100,000 cells compared to 1 in 12,500 in the BM MC population and 500 fold lower than the CD271$^+$ population. MSCs generated from CD271$^+$ cells, by adherence to plastic flasks, presented identical in vitro properties as MSCs generated from BM MNCs with expression of CD105$^+$ and capable of forming adipocytes and osteoblasts in vitro. Previous studies have demonstrated that MSC potential resides in the CD271$^+$CD45$^-$ cell population. Further, phenotypic analysis demonstrated that the CD271$^+$ cells were negative for typical MSC markers including CD105 and CD90, however, after culture the cells expressed classic MSC markers, CD105, CD90 and CD73. Further CD271 expression inhibits differentiation of MSCs to osteogenic, adipogenic, chondrogenic and myogenic lineages. The data herein, are consistent with the literature and support the proposal that CD271$^+$ cells are a stem cell population which is a precursor of MSCs and that differentiation of CD271$^+$ cells to plastic adherent MSCs results in commitment to adipogenic, chondrogenic and osteogenic lineages.

Additional experiments were performed in vitro to evaluate methodologies for generating MSCs under non adherent culture conditions. Given this laboratory's focus on cardiac repair it was hypothesized that MSC generated as plastic adherent cells may not be optimal for cardiac regeneration. In the BM, MSCs have the bone surface to act as a substrate for adherent cell growth, however, no equivalent substrate exists in the heart tissue. Therefore culture conditions were developed for expansion of MSCs under non adherent conditions (NA-MSCs). CD271$^+$ cells were cultured in teflon bags which minimized the adherence of cells a id regular massaging of the bags maintained the cells in suspension. As shown in the results section, MSCs proliferated in the bags forming spheres of cells with MSC properties, forming classic adherent MSC like cells when placed in standard plastic flasks and expressing CD105. The NA-MSCs also differentiated into adipocytes and chondrocytes under appropriate culture conditions. The osteogenic capacity of the NA-MSCs is currently being evaluated. In addition, it was demonstrated herein that the CD271$^+$ cells can be induced to express cardiac specific genes when cultured in the presence of media conditioned by murine heart derived stromal cells. Media conditioned by stromal cells derived from human fetal heart tissue also stimulates cardiac gene expression. These data evidence that the CD271$^+$ cells may have greater differentiation capacity compared to plastic adherent generated MSCs which failed to express cardiac genes when cultured under identical conditions.

The in vivo potential of human CD271$^+$ cells were evaluated in immuno compromised NOD/SCID mice after induction of a myocardial infarction. For comparison human MSCs isolated and expanded using standard adherence to plastic flasks were injected and a control group of animals that received injection of placebo. Injection of 120,000 CD271$^+$ cells resulted in improved cardiac function compared to mice injected with the equivalent number of MSCs and control animals with increased ejection fraction. Equivalent results were obtained for animals injected with a higher dose of MSCs. These data evidenced that the potential of CD271$^+$ cells is greater than MSCs at equivalent cells doses. In addition, expression of cardiac markers were detected in human cells in animals injected with CD271$^+$ cells but not animals injected with MSCs, consistent with the in vitro data demonstrating a cardiac potential of the CD271$^+$ cells but not the MSCs.

A number of groups have evaluated the potential of several bone marrow derived populations including mononuclear cells, CD34$^+$ cells, CD133$^+$ cells and MSCs. In this study, the potential of BM derived MSCs was evaluated in large animal preclinical studies and it was demonstrated that MSCs can engraft in and adjacent to chronic infarct scars and stimulate significant myocardial recovery including substantial reductions in infarct size, reverse remodeling of injured hearts, and increases in both myocardial contractility and tissue perfusion. These preclinical studies have led to ongoing clinical trials of MSCs at the University of Miami. One of these studies has been conducted in patients with chronic ischemic left ventricular dysfunction secondary to myocardial infarction who are undergoing cardiac surgery for coronary artery bypass grafting (CABG). Enrollment to this trial has been limited due to the urgency of patients to undergo bypass surgery and only a small number of patients are able to wait the 5 to 6 weeks needed to generate autologous MSCs. These BM derived CD271$^+$ cells represent an ideal autologous cell source for these patients. The CD271$^+$ cells can be isolated from a BM aspirate within 4 to 5 hours providing a readily available cell population for treatment of CABG patients who require urgent surgery. These studies provide evidence that BM-derived CD271$^+$ cells offer a unique cell population for study of cardiac repair. Compared to MSCs isolated by plastic adherence, the CD271$^+$ cells have a greater in vitro cardiac differentiation potential and treatment of mice following an MI result in greater improvement in cardiac function. The CD271 I cells can be isolated rapidly using magnetic cell selection, therefore could be a potential cell source for patients requiring bypass surgery.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A method of treating ischemic or myocardial tissue damage comprising:

isolating CD271$^+$ mesenchymal stem cell (MSC) precursors from bone marrow of a subject over a time period of no greater than 5 hours;

exposing the isolated CD271$^+$ MSC precursors to a demethylation agent, wherein the demethylation agent comprises one or more of 5-aza-2'-deoxycytidine, dimethylsulfoxide, chelerythrine chloride, retinoic acid or salts thereof, 2-amino-4-(ethylthio)butyric acid, procainamide, and procaine, and wherein exposure to the demethylation agent initiates differentiation among the CD271⁺ MSC precursors into at least one lineage selected from myocardial, vascular, and endothelial lineages;

parenterally administering to the heart of a patient multiple doses in increasing concentrations of a composition comprising at least one cytokine to form a chemotactic gradient; and parenterally administering to the patient a therapeutically effective amount of the isolated $CD271^+$ MSC precursors that were exposed to the demethylation agent.

2. The method of claim 1, wherein the $CD271^+$ MSC precursors are isolated from bone marrow mesenchymal cells that express low affinity nerve growth receptor CD271.

3. The method of claim 1, wherein the $CD271^+$ MSC precursors are isolated from one or more autologous, syngeneic, allogeneic, or xenogeneic donors.

4. The method of claim 1, wherein the $CD271^+$ MSC precursors differentiate into at least one of myocytes, cardiomyocytes, endothelial cells, myocardial cells, epicardial cells, vascular endothelial cells, and smooth muscle cells.

5. The method of claim 4, wherein the cardiomyocytes are identified by GATA-4, Nkx2.5, or $\alpha$-sarcomeric actin.

6. The method of claim 4, wherein the smooth muscle cells are identified by $\alpha$-smooth muscle actin or SMA22.

7. The method of claim 4, wherein the endothelial cells are identified by CD31 or vimentin.

8. The method of claim 1, wherein the $CD271^+$ MSC precursor cells differentiate into a plurality of lineages comprising: myocardial, vascular, and endothelial lineages.

9. The method of claim 1, further comprising administering one or more agents to the patient, the one or more agents comprising one or more chemotactic factors, growth factors, or differentiation factors.

10. The method of claim 1, where the ischemic or myocardial damage results from: heart failure, atherosclerosis, ischemia, myocardial infarction, transplantation, hypertension, restenosis, angina pectoris, rheumatic heart disease, or congenital cardiovascular defect.

11. The method of claim 1, wherein the $CD271^+$ MSC precursors are administered to the human patient in varying concentrations over a period of time.

12. The method of claim 1, wherein the $CD271^+$ MSC precursors are engrafted in a heart in vivo in infarct and border zones.

13. The method of claim 1, wherein $CD271^+$ MSC precursors are conditioned with media conditioned by heart derived stromal cells.

14. The method of claim 1, wherein the $CD271^+$ MSC precursors are cultured ex vivo, and non-adherent precursor mesenchymal stem cells (NA-MSCs) are isolated, expanded and administered to a patient.

15. The method of claim 1, wherein the parenteral administration is performed via injection of the $CD271^+$ MSC precursors onto or adjacent to the surface of the heart.

16. The method of claim 1, further comprising administering the $CD271^+$ MSC precursors with stem cells other than $CD271^+$ cells, myoblasts, myocytes, cardiomyoblasts, cardiomyocytes, or progenitors of myoblasts, myocytes, cardiomyoblasts, and/or cardiomyocytes.

17. A method of treating ischemic or myocardial tissue damage comprising:

isolating $CD271^+$ mesenchymal stem cell (MSC) precursors from bone marrow of a subject;

exposing the isolated $CD271^+$ MSC precursors to a demethylation agent, wherein the demethylation agent comprises one or more of 5-aza-2'-deoxycytidine, dimethylsulfoxide, chelerythrine chloride, retinoic acid or salts thereof, 2-amino-4-(ethylthio)butyric acid, procainamide, and procaine, and wherein exposure to the demethylation agent initiates differentiation among the MSC precursor cells into at least one lineage selected from myocardial, vascular, and endothelial lineages;

parenterally administering to the heart of a patient multiple doses in increasing concentrations of a composition comprising at least one cytokine to form a chemotactic gradient; and parenterally administering to the patient a therapeutically effective amount of the isolated $CD271^+$ MSC precursors that were exposed to the demethylation agent;

wherein the $CD271^+$ MSC precursors are administered as a matrix-cell complex.

18. The method of claim 17, wherein the matrix of the matrix-cell complex is a scaffold comprising at least the $CD271^+$ MSC precursors.

19. A kit for treatment of myocardial infarction, the kit comprising:

a first composition of bone marrow-derived $CD271^+$ mesenchymal stem cell (MSC) precursors prepared in a pharmaceutically acceptable form;

a second composition comprising at least one cytokine in a pharmaceutically acceptable form;

an applicator for each first and second composition; and instructions for use that follow the method of claim 1, wherein the pharmaceutically acceptable form for each first and second composition includes a pharmaceutically acceptable carrier.

* * * * *